(12) United States Patent
Zhang et al.

(10) Patent No.: US 8,501,401 B2
(45) Date of Patent: Aug. 6, 2013

(54) STEROIDOGENESIS MODIFIED CELLS AND METHODS FOR SCREENING FOR ENDOCRINE DISRUPTING CHEMICALS

(75) Inventors: Xiaowei Zhang, Saskatoon (CA); Markus Hecker, Saskatoon (CA); John P. Giesy, Saskatoon (CA)

(73) Assignee: University of Saskatchewan, Saskatoon, Saskatchewan ( * ) Notice: Subject to any disclaimer, the term of this patent is extended or adjusted under 35 U.S.C. 154(b) by 0 days.

(21) Appl. No.: 13/619,236

(22) Filed: Sep. 14, 2012

(65) Prior Publication Data
US 2013/0011850 A1 Jan. 10, 2013

Related U.S. Application Data

(63) Continuation of application No. 12/883,929, filed on Sep. 16, 2010, now Pat. No. 8,299,238.

(60) Provisional application No. 61/242,822, filed on Sep. 16, 2009.

(51) Int. Cl.
*C12Q 1/68* (2006.01)

(52) U.S. Cl.
USPC ............. 435/6; 435/325; 435/375; 536/24.5; 536/24.31; 536/24.1

(58) Field of Classification Search
None
See application file for complete search history.

(56) References Cited

U.S. PATENT DOCUMENTS
2003/0148519 A1 8/2003 Engelke et al.

OTHER PUBLICATIONS

Stocco, Douglas M. et al. Multiple Signaling Pathways Regulating Steroidogenesis and Steroidogenic Acute Regulatory Protein Expression: More Complicated than we Thought. Molecular Endocrinology. Nov. 2005, 19(11):2647-2659.
Nakamura, Y. et al., "Type 5 17 β-hydroxysteroid dehydrogenase (AKR1C3) contributes to testosterone production in the adrenal reticularis." 2009. The Journal of Clinical Endocrinology and Metabolism, vol. 94, pp. 2192-2198. ISSN: 0021-972X.
Hecker, M. et al., "Novel trends in endocrine disruptor testing: the H295R steroidogenesis assay for dentification of.inducers and inhibitors of hormone production." 2008. Analytical and Bioanalytical Chemistry, vol. 390, pp. 287-291. ISSN: 1618-2642.
Muller-Vieira, U. et al., "The adrenocortical tumour cell line NCI-H295R as an in vitro screening system for evaluation of CYP11B2 (aldosterone synthase) and CYP11B1 (steroid-11β-hydroxylase) inhibitors." 2005. Journal of Steroid Biochemistry and Molecular Biology, vol. 96, pp. 259-270. ISSN: 0960-0760.
Gracia, T. et al., "The H295R system for evaluation of endocrine disrupting effects." 2006. Ecotoxicology and Environmental Safety, vol. 65, pp. 293-305. ISSN: 0147-6513.
Zhang, X. et al., "Quantitative RT-PCR methods for evaluating toxicant-induced effects on steroidogenesis using the H295R cell line." 2005. Environmental Science and technology, vol. 39, pp. 2277-2785. ISSN: 0013-936X.
Gracia, T. et al., "Modulation of steroidogenic gene expression and hormone production of H295R cells by pharmaceuticals and environmentally active compounds." 2007. Toxicology and Applied Pharmacology, vol. 225, pp. 142-153. ISSN: 0041-008X.
Hecker et al., "Human adrenocarcinoma (H295R) cells for rapid in vitro determination of effects on steroidogenesis: Hormone production" 2006. Toxicology and Applied Pharmacology, vol. 217, pp. 114-124.
Hecker et al., "The OECD Validation Program of the H295R Steroidogenesis Assay for the Identification of in Vitro Inhibitors and Inducers of Testosterone and Estradiol Production. Phase 2: Inter-Laboratory Pre-Validation Studies" 2007. Env Sci Pollut Res 14, vol. 1, pp. 23-30.
Zhang et al. "Classification of Chemicals Based on Concentration-Dependent Toxicological Data Using ToxClust" 2009. Environmental Science & Technology, vol. 43, No. 10, pp. 3926-3932.
Staels, B., Hum, D. W., and Miller, W. L. (1993). Regulation of steroidogenesis in NCI-H295 cells: a cellular model of the human fetal adrenal. Mol Endocrinol 7(3), 423-433.
Gazdar et al. Establishment and Characterization of a Human Adrenocortical Carcinoma Cell Line That Expresses Multiple Pathways of Steroid Biosynthesis. Cancer Research 50, 5488-5496, Sep. 1, 1990.
Rainey et al. Regulation of Human Adrenal Carcinoma Cell (NCI-H295) Production of C19 Steroids. Journal of Clinical Endocrinology and Metabolism, 1993, vol. 77, 731-737 No. 3.
Rainey et al. The NCI-H295 cell line: a pluripotent model for human adrenocortical studies. Molecular and Cellular Endocrinology, 100 (1994) 45-50.
Fail, Patricia A. et al., Final Detailed Review Paper on Steroidogenesis Screening Assays and Endocrine Disruptors. U.S. Environmental Protection Agency (2005). Retrieved from http://www.epa.gov/endo/pubs/edmvs/steroidogenesis_drp_final_3_29_05.pdf.

(Continued)

*Primary Examiner* — Kimberly Chong
(74) *Attorney, Agent, or Firm* — Bereskin & Parr LLP; Carmela DeLuca; Patricia Folkins

(57) ABSTRACT

An isolated steroidogenesis modified cell comprising one or more steroid biosynthesis knock down nucleic acid operatively linked to a promoter, wherein the steroid biosynthesis knock down nucleic acid reduces the expression of a gene selected from the group CYP21A2, CYP11A1, CYP17A1, CYP19A1, 3-βHSD1, 3-βHSD2, 17-βHSD1, StAR, HMGR, CYP11B2, CYP11B1, 5α-Reductase 2, SULT1E1, CYP3A4 and UTG1A1, wherein the cell comprises reduced expression of one or more of said genes. The cells are useful for identifying endocrine disruptors. Accordingly, the disclosure includes in a further aspect a screening assay for identifying an endocrine disruptor comprising:
  a) contacting a cell described herein with a test substance;
  b) determining a level of at least one steroid or steroidogenic gene mRNA or enzyme activity;
wherein a modulation in the level of the at least one steroid or steroidogenic gene mRNA or enzyme activity compared to a control is indicative that the test substance is an endocrine disruptor.

34 Claims, 5 Drawing Sheets

OTHER PUBLICATIONS

Blaha et al. Alteration of steroidogenesis in H295R cells by organic sediment contaminants and relationships to other endocrine disrupting effects. Environment International 32 (2006) 749-757.

Ding et al. Effects of brominated flame retardants and brominated dioxins on steroidogenesis in h295r human adrenocortical carcinoma cell line. Environmental Toxicology and Chemistry, vol. 26, No. 4, pp. 764-772, 2007.

Gracia et al. Modulation of steroidogenesis by coastal waters and sewage effluents of Hong Kong, China, using the H295R assay. Environ. Sci. Pollut. Res. 2008.

Grund et al. The endocrine disrupting potential of sediments from the Upper Danube River (Germany) as revealed by in vitro bioassays and chemical analysis. Environ. Sci. Pollut. Res (2011) 18:446-460.

He et al. Effects of 20 PBDE metabolites on steroidogenesis in the H295R cell line., Toxicology Letters 176 (2008) 230-238.

He et al. Ozonation attenuates the steroidogenic disruptive effects of sediment free oil sands process water in the H295R cell line., Chemosphere 80 (2010) 578-584.

Hecker et al. Multi-Laboratory Validation of the H295R Steroidogenesis Assay to Identify Modulators of Testosterone and Estradiol Production. U.S. Environmental Protection Agency (2008). Retrieved from http://www.epa.gov/endo/pubs/h295r_validation_study_interim_report.pdf.

Hecker et al. The OECD validation program of the H295R steroidogenesis assay: Phase 3. Final inter-laboratory validation study., Environ. Sci. Pollut. Res (2011) 18:503-515.

Higley et al. Assessment of chemical effects on aromatase activity using the H295R cell line. Environ Sci Pollut Res (2010) 17:1137-1148.

Hilscherova et al. Assessment of the Effects of Chemicals on the Expression of Ten Steroidogenic Genes in the H295R Cell Line Using Real-Time PCR. Toxicological Sciences 81, 78-89 (2004).

Kavlock et al. Research Needs for the Risk Assessment of Health and Environmental Effects of Endocrine Disruptors: A Report of the U.S. EPA-sponsored Workshop. Environmental Health Perspectives, vol. 104, Supplement 4, Aug. 1996.

Liu et al. Effects of fluorotelomer alcohol 8:2 FTOH on steroidogenesis in H295R cells: Targeting the cAMP signalling cascade. Toxicology and Applied Pharmacology, 247 (2010), 222-228.

Ma et al. Modulation of steroidogenic gene expression and hormone synthesis in H295R cells exposed to PCP and TCP. Toxicology, 282 (2011), 146-153.

OECD (2002), Detailed Review Paper Appraisal of Test Methods for Sex Hormone Disrupting Chemicals, OECD Series on Testing and Assessment, No. 21, OECD Publishing; doi: 10.1787/9789264078383-en.

Sanderson, Thomas J. The Steroid Hormone Biosynthesis Pathway as a Target for Endocrine-Disrupting Chemicals. Toxicological Sciences 94(1), 3-21 (2006).

Sanderson et al. 2-Chloro-s-Triazine Herbicides Induce Aromatase (CYP19) Activity in H295R Human Adrenocortical Carcinoma Cells: A Novel Mechanism for Estrogenicity? Toxicological Sciences 54, 121-127 (2000).

Sanderson et al. Induction and Inhibition of Aromatase (CYP19) Activity by Various Classes of Pesticides in H295R Human Adrenocortical Carcinoma Cells. Toxicology and Applied Pharmacology 182, 44-54 (2002).

Song et al. Effects of fifteen PBDE metabolites, DE71, DE79 and TBBPA on steroidogenesis in the H295R cell line. Chemosphere 71 (2008) 1888-1894.

Villeneuve et al. Comparison of fathead minnow ovary explant and H295R cell-based steroidogenesis assays for identifying endocrine-active chemicals. Ecotoxicology and Environmental Safety 68 (2007) 20-32.

Xu et al. Effects of PCBs and MeSO2—PCBs on adrenocortical steroidogenesis in H295R human adrenocortical carcinoma cells. Chemosphere 63 (2006) 772-784.

Doghman et al. Increased Steroidogenic Factor-1 Dosage Triggers Adrenocortical Cell Proliferation and Cancer. Molecular Endocrinology, vol. 21, p. 2968-2987, 2007.

SEQUENCE LISTING

```
<160> NUMBER OF SEQ ID NOS: 15

<210> SEQ ID NO 1
<211> LENGTH: 58
<212> TYPE: DNA
<213> ORGANISM: Homo sapiens

<400> SEQUENCE: 1
ccggcgacaa cttaatgcct gcctactcga gtaggcaggc attaagttgt cgtttttg      58

<210> SEQ ID NO 2
<211> LENGTH: 97
<212> TYPE: DNA
<213> ORGANISM: Homo sapiens

<400> SEQUENCE: 2
tgctgttgac agtgagcgac ctgcagagat atcttgtaaa tagtgaagcc acagatgtat    60
ttacaagata tctctgcagg gtgcctactg cctcgga                             97

<210> SEQ ID NO 3
<211> LENGTH: 97
<212> TYPE: DNA
```

<213> ORGANISM: Homo sapiens

<400> SEQUENCE: 3
tgctgttgac agtgagcgcg ggcacagaag ttatcatcaa tagtgaagcc acagatgtat    60
tgatgataac ttctgtgccc ttgcctactg cctcgga                              97

<210> SEQ ID NO 4
<211> LENGTH: 97
<212> TYPE: DNA
<213> ORGANISM: Homo sapiens

<400> SEQUENCE: 4
tgctgttgac agtgagcgaa gaaccaggct acaagagaaa tagtgaagcc acagatgtat    60
ttctcttgta gcctggttct ctgcctactg cctcgga                              97

<210> SEQ ID NO 5
<211> LENGTH: 58
<212> TYPE: DNA
<213> ORGANISM: Homo sapiens

<400> SEQUENCE: 5
ccggcgcctg tatcattgat gtcttctcga aagacatca atgatacagg cgttttg         58

<210> SEQ ID NO 6
<211> LENGTH: 97
<212> TYPE: DNA
<213> ORGANISM: Homo sapiens

<400> SEQUENCE: 6
tgctgttgac agtgagcgac cacacagtca cattatcaaa tagtgaagcc acagatgtat    60
ttgataatgt gactgtgtgg ctgcctactg cctcgga                              97

<210> SEQ ID NO 7
<211> LENGTH: 97
<212> TYPE: DNA
<213> ORGANISM: Homo sapiens

<400> SEQUENCE: 7
tgctgttgac agtgagcgcg ggtggctaat taagatagat tagtgaagcc acagatgtaa    60
tctatcttaa ttagccaccc atgcctactg cctcgga                              97

<210> SEQ ID NO 8
<211> LENGTH: 58
<212> TYPE: DNA
<213> ORGANISM: Homo sapiens

<400> SEQUENCE: 8
ccgggctgcc caagagcatc atcaactcga gttgatgatg ctcttgggca gcttttg        58

<210> SEQ ID NO 9
<211> LENGTH: 58
<212> TYPE: DNA
<213> ORGANISM: Homo sapiens

<400> SEQUENCE: 9
ccgggcagtg ataaaggagg catttctcga gaaatgcctc ctttatcact gcttttg        58

<210> SEQ ID NO 10
<211> LENGTH: 58
<212> TYPE: DNA
<213> ORGANISM: Homo sapiens -continued

```
<400> SEQUENCE: 10
ccggcctcac tttcagagcg attaactcga gttaatcgct ctgaaagtga ggtttttg        58

<210> SEQ ID NO 11
<211> LENGTH: 58
<212> TYPE: DNA
<213> ORGANISM: Homo sapiens

<400> SEQUENCE: 11
ccggccctca acagtacacc agcatctcga gatgctggtg tactgttgag ggtttttg        58

<210> SEQ ID NO 12
<211> LENGTH: 58
<212> TYPE: DNA
<213> ORGANISM: Homo sapiens

<400> SEQUENCE: 12
ccggcctcaa gatgtttgag gactactcga gtagtcctca aacatcttga ggtttttg        58

<210> SEQ ID NO 13
<211> LENGTH: 58
<212> TYPE: DNA
<213> ORGANISM: Homo sapiens

<400> SEQUENCE: 13
ccggccagaa attgtcgccc ttcatctcga gatgaagggc gacaatttct ggtttttg        58

<210> SEQ ID NO 14
<211> LENGTH: 58
<212> TYPE: DNA
<213> ORGANISM: Homo sapiens

<400> SEQUENCE: 14
ccggccttac atatacacac cctttctcga gaaagggtgt gtatatgtaa ggtttttg        58

<210> SEQ ID NO 15
<211> LENGTH: 58
<212> TYPE: DNA
<213> ORGANISM: Homo sapiens

<400> SEQUENCE: 15
ccggcccact gtattcttct tgcatctcga gatgcaagaa gaatacagtg ggtttttg        58
```

STEROIDOGENESIS MODIFIED CELLS AND METHODS FOR SCREENING FOR ENDOCRINE DISRUPTING CHEMICALS

RELATED APPLICATIONS

This application is a continuation of U.S. application Ser. No. 12/883,929, filed on Sep. 16, 2010, which claims priority to U.S. Provisional Application No. 61/242,822, filed Sep. 16, 2009, each of which are incorporated herein by reference in their entirety.

INCORPORATION OF SEQUENCE LISTING

A computer readable form of the Sequence Listing "13764-187_SequenceListing.txt" (2913 bytes), created Sep. 14, 2012, is herein incorporated by reference.

FIELD OF THE DISCLOSURE

The disclosure relates to steroidogenesis modified cells such as modified H295R cells which are modified to reduce the expression of one or more enzymes (knocked down) involved in steroidogenesis. The disclosure also relates to methods, uses and compositions comprising these cells for identifying endocrine disrupting substances.

BACKGROUND OF THE DISCLOSURE

Over the past two decades, there has been increasing concern about the possible effects of exposure to chemicals in the environment on endocrine and reproductive systems in humans and wildlife (Kavlock et al. 1996). To address these concerns, national and international programs have been initiated to develop new guidelines for the screening and testing of potential endocrine-disrupting chemicals (EDCs) in vertebrates. The Safe Drinking Water Act Amendments of 1995 and the Food Quality Protection Act of 1996 mandate screening for endocrine-disrupting properties of chemicals in drinking water or pesticides used in food production. In response to this legislation, the federal Endocrine Disrupter Screening and Testing Advisory Committee (EDSTAC) has identified disrupting the process of steroidogenesis as one of the important toxicity pathways of endocrine disruption in addition to binding to three key endocrine nuclear receptors, i.e. estrogen receptors (ER), androgen receptors (AR) and thyroid hormone receptor (ThR) (Hilscherova et al. 2004; Sanderson et al. 2002; Zhang et al. 2005). The human H295R adrenocarcinoma cell-based steroidogenesis assay has been approved by the United States Environmental Protection Agency (USEPA) for use in Tier I of the Endocrine Disruptor Screening Program (EDSP) and is currently in the last phase of validation through OECD as an international standard to test chemicals for endocrine disrupting effects. While previously used assays have used production of different mRNAs as endpoints, currently used assays use as endpoints the production and release to the medium of the steroid hormones testosterone (T) and 17β-estradiol (E2) (Hecker et al. 2006).

H295R cells express genes that encode for all the key enzymes involved in steroidogenesis (FIG. 1) (Gazdar et al. 1990; Staels et al. 1993; Rainey et al. 1994). This is a unique property, because in vivo expression of these genes is tissue- and developmental stage-specific with no one tissue or developmental stage simultaneously expressing all of the genes involved in steroidogenesis. H295R cells have physiological characteristics of zonally undifferentiated human fetal adrenal cells. H295R cells represent a unique in vitro system with the ability to produce the steroid hormones found in the adult adrenal cortex and the gonads, which allows testing for effects on both corticosteroid synthesis and the production of sex steroid hormones such as androgens and estrogens.

One of the key hormones of interest, E2, is produced by H295R cells at relatively small and varying concentrations (~10-50 pg E2/ml in culture medium) that are difficult to measure by use of automated ELISA or the more laborious LC\MS-MS method. Concentrations of E2 released by H295R cells into the medium are near the current limit of quantification (LOQ, approximately 2-10 pg E2/ml), which makes it difficult to measure reductions in E2 release caused by EDCs. The relatively great variance in E2 production around the detection limit is also a limiting factor. In addition, due to the small basal concentrations released by the H295R cells into the medium, it is difficult to demonstrate a decrease in production, which is also important for use as a screening tool. This is especially true with regard to the assessment of weak inhibitors.

Another endpoint of interest in screening for potential endocrine disruption is changes in expression of the aromatase (CYP19) gene, protein and enzyme activity, the enzyme that transforms (aromatizes) Testosterone to E2.

SUMMARY OF THE DISCLOSURE

In an aspect, the disclosure provides an isolated steroidogenesis modified cell comprising a steroid biosynthesis knock down nucleic acid operatively linked to a promoter, wherein the steroid biosynthesis knock down nucleic acid reduces the expression of a gene selected from the group CYP21A2, CYP11A1, CYP17A1, CYP19A1, 3-βHSD1, 3-βHSD2, 17-βHSD1, StAR, HMGR, CYP11B2, CYP11B1, 5α-Reductase 2, SULT1E1, CYP3A4 and UTG1A1 wherein the cell comprises reduced expression of one or more of said genes.

In an embodiment, the knock down nucleic acid comprises a siRNA nucleic acid, a shRNA nucleic acid or an antisense nucleic acid.

In an embodiment, the one or more genes comprises CYP21A2. In an embodiment, the steroid biosynthesis knock down nucleic acid comprises CCGGCGACAACTTAATGC-CTGCCTACTCGAGTAGGCAGGCATTAAGTTGTC GTTTTTG (SEQ ID NO:1).

In an embodiment, the one or more genes comprises CYP11A1. In an embodiment, the steroid biosynthesis knock down nucleic acid comprises TGCTGTTGACAGTGAGC-GACCTGCAGAGATATCTTGTAAATAGTGAAGCCA CAGATGTATTTACAAGATATCTCTG-CAGGGTGCCTACTGCCTCGGA (SEQ ID NO:2).

In an embodiment, the one or more genes comprises CYP17A1. In an embodiment, the steroid biosynthesis knock down nucleic acid comprises TGCTGTTGACAGT-GAGCGCGGGCACAGAAGTTATCATCAAT-AGTGAAGCCA CAGATGTATTGATGATAACTTCTGT-GCCCTTGCCTACTGCCTCGGA (SEQ ID NO:3).

In an embodiment, the one or more genes comprises CYP19A1. In an embodiment, the steroid biosynthesis knock down nucleic acid comprises TGCTGTTGACAGTGAGC-GAAGAACCAGGCTACAAGAGAAATAGTGAAGCCA CAGATGTATTTCTCTTGTAGCCTGGT-TCTCTGCCTACTGCCTCGGA (SEQ ID NO:4).

In an embodiment, the one or more genes comprises 3-βHSD1. In an embodiment, the steroid biosynthesis knock down nucleic acid comprises CCGGCGCCTGTATCAT-TGATGTCTTCTCGAGAAGACATCAATGATACAGGC GTTTTTG (SEQ ID NO:5).

In an embodiment, the one or more genes comprises 3-βHSD2. In an embodiment, the steroid biosynthesis knock down nucleic acid comprises TGCTGTTGACAGTGAGC-GACCACACAGTCACATTATCAAATAGTGAAGCCA CAGATGTATTTGATAATGTGACTGTGTG-GCTGCCTACTGCCTCGGA (SEQ ID NO:6).

In an embodiment, the one or more genes comprises 17-βHSD1. In an embodiment, the steroid biosynthesis knock down nucleic acid comprises TGCTGTTGACAGT-GAGCGCGGGTGGCTAATTAAGATAGATT-AGTGAAGCCA CAGATGTAATCTATCTTAATTAGC-CACCCATGCCTACTGCCTCGGA (SEQ ID NO:7).

In an embodiment, the one or more genes comprises StAR. In an embodiment, the steroid biosynthesis knock down nucleic acid comprises CCGGGCTGCCCAAGAGCAT-CATCAACTCGAGTTGATGATGCTCTTGGGCA GCTTTTTG (SEQ ID NO:8).

In an embodiment, the one or more genes comprises HMGR. In an embodiment, the steroid biosynthesis knock down nucleic acid comprises CCGGGCAGTGATAAAG-GAGGCATTTCTCGAGAAATGCCTCCTTTATCACTG CTTTTT (SEQ ID NO:9).

In an embodiment, the one or more genes comprises CYP11B2. In an embodiment, the steroid biosynthesis knock down nucleic acid comprises CCGGCCTCACTTTCA-GAGCGATTAACTCGAGTTAATCGCTCT-GAAAGTGAG GTTTTTG (SEQ ID NO:10).

In an embodiment, the one or more genes comprises CYP11B1. In an embodiment, the steroid biosynthesis knock down nucleic acid comprises CCGGCCCTCAACAGTA-CACCAGCATCTCGAGATGCTGGTGTACTGTTGAGG GTTTTTG (SEQ ID NO:11).

In an embodiment, the one or more genes comprises 5α-Reductase 2. In an embodiment, the steroid biosynthesis knock down nucleic acid comprises CCGGCCTCAAGAT-GTTTGAGGACTACTCGAGTAGTCCT-CAAACATCTTGAG GTTTTTG (SEQ ID NO:12).

In an embodiment, the one or more genes comprises SULT1E1. In an embodiment, the steroid biosynthesis knock down nucleic acid comprises CCGGCCAGAAATTGTCGC-CCTTCATCTCGAGATGAAGGGCGACAATTTCTG GTTTTTG (SEQ ID NO:13).

In an embodiment, the one or more genes comprises CYP3A4. In an embodiment, the steroid biosynthesis knock down nucleic acid comprises CCGGCCTTACATATACA-CACCCTTTCTCGAGAAAGGGTGTGTATATGTAAG GTTTTTG (SEQ ID NO:14).

In an embodiment, the one or more genes comprises UGT1A1. In an embodiment, the steroid biosynthesis knock down nucleic acid comprises CCGGCCCACTGTATTCT-TCTTGCATCTCGAGATGCAAGAAGAATACAGTGG GTTTTTG (SEQ ID NO:15).

In an embodiment, the isolated steroidogenesis modified cell is an isolated steroidogenesis H295R modified cell.

In an embodiment, the isolated steroidogenesis modified cell is an isolated steroidogenesis H295, JEG-3 or R2C modified cell.

In an embodiment, the isolated steroidogenesis modified H295R cell comprises a CYP21A2 knock down nucleic acid operatively linked to a promoter, wherein the CYP21A2 knock down nucleic acid reduces the expression of CYP21A2.

In an embodiment, the isolated steroidogenesis modified H295R cell comprises a CYP17A1] knock down nucleic acid operatively linked to a promoter, wherein the CYP17A1 knock down nucleic acid reduces the expression of CYP17A1.

In an embodiment, the isolated steroidogenesis modified H295R cell comprises a CYP19A1 knock down nucleic acid operatively linked to a promoter, wherein the CYP19A1 knock down nucleic acid reduces the expression of CYP19A1.

In another aspect, the disclosure further provides a screening assay for identifying an endocrine disruptor comprising: a) contacting a steroidogenesis cell such as a steroidogenesis modified H295R cell of the present disclosure with a test substance; b) determining a level of at least one steroid or steroidogenic gene expression product, e.g. mRNA or protein, or enzyme activity; wherein a modulation in the level of the at least one steroid or steroidogenic gene expression product or enzyme activity compared to a control is indicative that the test substance is an endocrine disruptor.

A further aspect includes a kit for screening for an endocrine disruptor comprising a steroidogenesis cell described herein and a component for determining the level of at least one steroid.

In yet a further aspect, the disclosure provides a system for predicting the mechanism of action of an endocrine disruptor with unknown mechanism comprising: (i) a control module for receiving a steroid production profile for the endocrine disruptor wherein the steroid production profile is obtained by contacting the endocrine disruptor with a steroidogenesis cell such as a steroidogenesis modified H295R cell disclosed herein and determining a level of at least one steroid or steroidogenic gene expression product or activity produced by the cell line; (ii) a database comprising steroid production profiles for a plurality of reference endocrine disruptors; (iii) analysis module for comparing the steroid production profile of the endocrine disruptor with the steroid production profiles of the plurality of reference endocrine disruptors; and for identifying a best match for the steroid production profile of the endocrine disruptor with the steroid production profiles of the plurality of reference endocrine disruptors, wherein the mechanism of action of the best match reference endocrine disruptor is predicted to be the mechanism of action of the endocrine disruptor.

Other features and advantages of the present disclosure will become apparent from the following detailed description. It should be understood, however, that the detailed description and the specific examples while indicating preferred embodiments of the disclosure are given by way of illustration only, since various changes and modifications within the spirit and scope of the disclosure will become apparent to those skilled in the art from this detailed description.

DETAILED DESCRIPTION OF THE DISCLOSURE

I. Definitions

Figure 1:
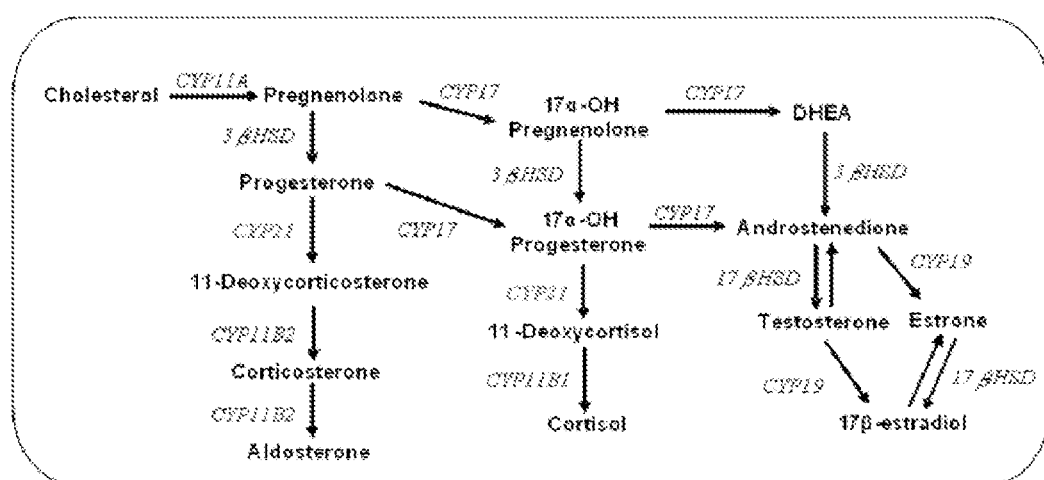
FIG. 1 Steroidogenesis pathways in H295R cells. CYP11A, desmolase (20,22 Desmolase); CYP17, steroid 17α-hydroxylase; CYP21, steroid 21-hydroxylase; CYP19, aromatase; 3βHSD, 3β-hydroxysteroid dehydrogenase; CYP11B1, steroid 11β hydroxylase, CYP11B2, aldosterone synthetase; 17βHSD, 17β hydroxysteroid dehydrogenase. The enzyme CYP21 encoded by human CYP21A2 gene is highlighted.

As used herein "a", "an" and/or "the" includes one and/or more than one.

The term "endocrine disrupting chemical" or "endocrine disrupting compound" also referred to as "endocrine disruptor" or "hormonally active agent" as used herein refers to an exogenous substance that interferes with the synthesis, secretion, transport, binding, action, or elimination of endogenous hormones in vertebrates including human and/or invertebrates (mollusks, crustacean, etc.). Endocrine disrupting compounds include a number of chemical classes, including for example, pesticides, compounds used in the plastics industry and in consumer products, compounds used as food additives and in cosmetics and other industrial by-products, pharmaceuticals, naturally occurring hormones (e.g., phytoestrogens), degradation products and metabolites of any of these classes of compounds and by-products of manufacture, and pollutants.

The term "steroidogenesis cell" as used herein refers to any cell, modified or unmodified that produces one or more steroid hormones including sex steroids, mineral- and corticosteroids. Specifically, these include estrogens (17beta-estradiol, estrone) and androgens (testosterone, androstenedione, dihydrotestosterone), as well as the mineral- and corticosterdoids and/or their precursors, and includes for example a H295R cell, a steroidogenesis modified H295 cell, a steroidogenesis modified H295R cell, a JEG-3, a R2C cell, a steroidogenesis modified JEG-3 cell and a steroidogenesis modified R2C cell.

The term "steroidogenesis modified H295R cell" as used herein refers to a H295R cell that has been modified by, for example, recombinant technology to knock down the gene expression of one or more genes involved in a steroidogenesis pathway e.g. a steroid biosynthesis gene, including but not limited to the following genes: CYP21A2, CYP11A1, CYP17A1, CYP19A1, 3-βHSD1, 3-βHSD2, 17-βHSD1, StAR, HMGR, CYP11B2, CYP11B1, 5α-Reductase 2, SULT1E1, UGT1A1 and CYP3A4. For example, the expression of two or more of the genes listed above can be knocked down simultaneously or contemporaneously e.g. using a construct that produces two or more siRNA nucleic acids, each targeting a gene involved in a steroidogenesis pathway, or two or more of the genes can be knocked down sequentially. For example, a H295R cell modified to knock down gene expression of CYP21A2 can be further modified to knock down expression of another gene, for example CYP11A1. Further, for example, the expression of related steroidogenesis gene family members could also be knocked down to produce steroidogenesis modified cells. For example, if a new steroidogenesis gene for example a new CYP21 subfamily gene were identified, also involved in steroidogenesis, and/or if a steroidogeneis cell to be modified expressed additional steroidogenesis genes other than the specific ones mentioned herein e.g. additional CYP21 family members, the expression of one or more of these genes could also be knocked down to produce a cell useful for the methods described herein.

The term "steroidogenesis modified H295 cell" as used herein refers to a H295 cell that has been modified by for example, recombinant technology to knock down the gene expression of one or more genes involved in a steroidogenesis pathway e.g. a steroid biosynthesis gene, including but not limited to the following genes: CYP21A2, CYP11A1, CYP17A1, CYP19A1, 3-βHSD1, 3-βHSD2, 17-βHSD1, StAR, HMGR, CYP11B2, CYP11B1, 5α-Reductase 2, SULT1E1, UGT1A1 and CYP3A4. For example, the expression of two or more of the genes listed above can be knocked down simultaneously or contemporaneously e.g. using a construct that produces two or more siRNA nucleic acids, each targeting a gene involved in a steroidogenesis pathway, or two or more of the genes can be knocked down sequentially. For example, a H295 cell modified to knock down gene expression of CYP21A2 can be further modified to knock down expression of another gene, for example CYP11A1.

Similarly, the term "steroidogenesis modified JEG-3 cell" as used herein refers to a JEG-3 cell that has been modified by for example, recombinant technology to knock down the gene expression of one or more genes involved in a steroidogenesis pathway e.g. a steroid biosynthesis gene, including but not limited to the following genes: CYP21A2, CYP11A1, CYP17A1, CYP19A1, 3-βHSD1, 3-βHSD2, 17-βHSD1, StAR, HMGR, CYP11B2, CYP11B1, 5α-Reductase 2, SULT1E1, UGT1A1 and CYP3A4 and the term "steroidogenesis modified R2C cell" as used herein refers to a R2C cell that has been modified by for example, recombinant technology to knock down the gene expression of one or more genes involved in a steroidogenesis pathway e.g. a steroid biosynthesis gene, including but not limited to the following genes: CYP21A2, CYP11A1, CYP17A1, CYP19A1, 3-βHSD1, 3-βHSD2, 17-βHSD1, StAR, HMGR, CYP11B2, CYP11B1, 5α-Reductase 2, SULT1E1, UGT1A1 and CYP3A4.

The term "modified" as used herein in terms of a steroidogenesis modified cell means genetically altering the cell, for example by recombinant technology, to knock down and/or reduce with the expression of one or more genes involved in a steroidogenesis pathway. This can for example be accomplished by antisense technology and/or replacing the gene by homologous recombination with a variant that exhibits decreased expression for example because of a weaker promoter etc.

The term "a steroid biosynthesis gene" as used herein refers to a gene involved in a steroidogenesis pathway and includes but is not limited to a gene selected from CYP21A2, CYP11A1, CYP17A1, CYP19A1, 3-βHSD1, 3-βHSD2, 17-βHSD1, StAR, HMGR, CYP11B2, CYP11B1, 5α-Reductase 2, SULT1E1, UGT1A1 and CYP3A4 (for example see FIG. 1, Table 1).

The term "CYP21A2" also known as "steroid 21-hydroxylase" or "21-hydroxylase" and optionally "CYP21" or "CYP21B" refers to cytochrome P450, family 21, subfamily A, polypeptide 2, preferably human to cytochrome P450, family 21, subfamily A polypeptide 2, for example as disclosed in Entrez GeneID1589.

The term "CYP11A1" also referred to as "desmolase" or "20,22 Desmolase" refers to a cytochrome P450 family 11, subfamily A polypeptide 1, preferably human cytochrome P450 family 11, subfamily A polypeptide 1, for example as disclosed in Entrez Gene ID 1583.

The term "CYP17A1" is for example also referred to as steroid 17α-hydroxylase, CYP17A and CYP17.

The term "CYP19A1" is for example also referred to as aromatase, "CYP19", "CYP19A", and "-450AROM", for example as disclosed in Entrez GeneID1588.

The terms "3βHSD1" also referred to for example as "Type 1 3βHSD", "3βHSD", 3β-hydroxysteroid dehydrogenase Type 1 or 3β-hydroxysteroid dehydrogenase, for example as disclosed in Entrez GeneID3283.

The term "3βHSD2" is also for example referred to as The term "3βHSD2" also referred to as "Type 2 3βHSD", "3βHSD", "HSD3B2", 3β-hydroxysteroid dehydrogenase Type 2 or 3β-hydroxysteroid dehydrogenase, for example as disclosed in Entrez 3284.

The term "CYP11B1" is also for example referred to "P450C11", steroid 11β hydroxylase, for example as disclosed in Entrez GeneID1584.

The term "CYP11B2" is also referred to for example as "P450C18", aldosterone synthetase, for example as disclosed in Entrez GeneID1585.

The term "17βHSD1" is also for example referred to as "17βHSD", 17β hydroxysteroid dehydrogenase Type 1 or 17β hydroxysteroid dehydrogenase, for example as disclosed in Entrez GeneID3292.

The term "StAR" is also for example referred to as steroidogenic acute regulatory protein, for example as disclosed in Entrez Gene ID: 6770.

The term "HMGR" is also for example referred to as "HMGCR", 3-hydroxy-3-methylglutaryl-coenzyme A reductase, for example as disclosed in Entrez Gene ID: 3156.

The term "SULT1E1" is also for example referred to as "EST-1", "EST", 5α-Reductase 2, estrogen-preferring sulfotransferas, for example as disclosed in Entrez GeneID6783.

The term "CYP3A4" is also for example referred to as "CYP3A", "P450C3", cytochrome P450 family 3 subfamily A polypeptide 4, for example as disclosed in Entrez GeneID1576.

The term "UGT1A1" is also for example referred to as "UGT1A1" also referred to as "UGT1", "UDPGT", UDP-glucuronosyltransferase, for example as disclosed in Entrez GeneID54658.

The term "steroidogenesis pathway" as used herein refers to the genes, enzymes, substrates, intermediates and final products involved in steroid biosynthesis including for example corticosteroid synthesis, including mineralo- and gluco-corticosteroids such as aldosterone and cortisol respectively, and the production of sex steroid hormones such as androgens and estrogens.

The term "steroidogenesis gene" or "steroid by synthesis gene" refers to a gene selected from CYP21A2, CYP11A1, CYP17A1, CYP19A1, 3-βHSD1, 3-βHSD2, 17-βHSD1, StAR, HMGR, CYP11B2, CYP11B1, 5α-Reductase 2, SULT1E1, UGT1A1 and CYP3A4.

The term "steroid biosynthesis knockdown nucleic acid" refers to a nucleic acid molecule that is specific for reducing or "knocking down" the expression of a steroid biosynthesis gene, such as a gene selected from CYP21A2, CYP11A1, CYP17A1, CYP19A1, 3-βHSD1, 3-βHSD2, 17-βHSD1, StAR, HMGR, CYP11B2, CYP11B1, 5α-Reductase 2, SULT1E1, UGT1A1 and CYP3A4. For example, expression of a steroid biosynthesis gene can be reduced by introducing a small interfering RNA (siRNA), small hairpin RNA or short hairpin RNA (shRNA), or antisense nucleic acid that is specific for the steroid biosynthesis gene. Reference to a specific knockdown nucleic acid that targets a gene is made by referring to the gene being knocked down such that for example, a CYP21A2 knockdown nucleic acid refers to a steroid biosynthesis knockdown nucleic acid that reduces expression of CYP21A2, and a StAR knockdown nucleic acid refers to a steroid biosynthesis knockdown nucleic acid that reduces expression of StAR. Several genes can for example be targeted simultaneously, and/or several regions of a single gene can be targeted, for example multiple RNAi can be accomplished by introducing multiple steroid biosynthesis knockdown nucleic acids (e.g. multiple siRNA or shRNA species), for example by transfection and/or viral transfer. Alternatively, a construct with several consecutive steroid biosynthesis knockdown nucleic acids (e.g. each optionally operatively linked to a promoter) or expression of a composite steroid biosynthesis knockdown nucleic acid (e.g. RNA) comprising several consecutive steroid biosynthesis knockdown nucleic acids that is cleaved into multiple shRNAs (e.g. individual steroid biosynthesis knockdown nucleic acids) can be used.

The term "a cell" as used herein includes a plurality of cells and includes a cell line.

The term an "isolated cell" as used herein refers to a cell or population of cells including a cell line that has been removed from the environment in which the cell occurs naturally and/or that have been modified from the state in which the cell occurs in its natural environment.

The term "H295R" or "NCI-H295R" as used herein refers to a strain of H295 cells selected for attachment to culture dishes and which are a pluripotent human adrenocortical carcinoma cell line that expresses genes that encode all the key enzymes involved in steroidogenesis. H295R is publicly available from, for example the American Type Culture Collection (ATCC). The term H295R also includes sub-strains and sub-clones of H295R cells. H295R cells are derived from H295 cells which also express all of the key enzymes involved in steroidogenesis (Gazdar et al. 1990; Staels et al. 1993; Rainey et al. 1994). As H295R cells are a strain of H295 cells, a person skilled in the art would recognize that parental H295 cells and other strains thereof can also be used to make the modified cells of the disclosure for use for example in screening assays described herein. Accordingly, the disclosure is intended to encompass steroidogenesis modified H295 cells, the making of such cells and the use of steroidogenesis modified H295 cells in the methods disclosed herein.

The term "cell line" as used herein refers to a group of genetically uniform immortal cells that be propagated in vitro for an indefinite term. The cell line can derive from a single clone (e.g., monoclonal cell line) or from more than one clone (e.g., polyclonal cell line).

The term "stable cell line" as used herein refers to a cell line that shows consistent growth and/or maintenance of one or more parameters or introduced properties, for example, maintenance of puromycin resistance (e.g., which is a proxy for maintenance of a construct comprising the puromycin-resistance gene) after multiple freeze-thaw cycles.

The term "selection marker nucleic acid" as used herein refers to a nucleic acid that encodes a marker, such as an antibiotic resistance marker such as a puromycin resistance gene, which are well known in the art.

The term "selection marker" as used herein refers to a gene introduced into a cell that confers a trait suitable for artificial selection. Selection markers are often antibiotic resistance genes, such as puromycin resistance gene or neomycin resistance gene. Selection markers function as a type of reporter to indicate the success of a transfection or other procedure meant to introduce foreign DNA into a cell.

The term "nucleic acid" and/or "oligonucleotide" as used herein refers to a sequence of nucleotide or nucleoside monomers consisting of naturally occurring bases, sugars, and intersugar (backbone) linkages, and includes single-stranded and double-stranded molecules, RNA and DNA. The term also includes modified or substituted oligomers comprising non-naturally occurring monomers or portions thereof, which function similarly, which are referred to herein as "chemical analogues" and/or "oligonucleotide analogues" such as "peptide nucleic acids". Such modified or substituted nucleic acids may be preferred over naturally occurring forms because of properties such as enhanced cellular uptake or increased stability in the presence of nucleases. The term also includes chimeric nucleic acids that contain two or more chemically distinct regions. For example, chimeric nucleic acids may contain at least one region of modified nucleotides that confer beneficial properties (e.g., increased nuclease resistance, increased uptake into cells), or two or more nucleic acids of the disclosure may be joined to form a chimeric nucleic acid. The term "nucleic acid" includes, for example, "antisense nucleic acids or oligonucleotides", "siRNA nucleic acids or oligonucleotides", "shRNA oligonucleotides" and "miRNA" as well as oligonucleotide analogues such as "morpholino oligonucleotides", "phosphorothioate oligonucleotides", and "peptide nucleic acids". The term "nucleic acid" also includes aptamers.

The term "isolated nucleic acid" or "isolated nucleic acid molecule" as used herein refers to a nucleic acid substantially free of cellular material or culture medium when produced by recombinant DNA techniques, or chemical precursors, or other chemicals when chemically synthesized. An isolated nucleic acid is also substantially free of sequences which naturally flank the nucleic acid (i.e. sequences located at the 5' and 3' ends of the nucleic acid) from which the nucleic acid is derived.

An "antisense nucleic acid" or "antisense oligonucleotide" comprises a nucleotide sequence, which is complementary to a "sense" nucleic acid encoding a protein, e.g., complementary to the coding strand of a double-stranded cDNA molecule or complementary to a messenger RNA (mRNA) sequence. Accordingly, an antisense nucleic acid can hydrogen bond to a sense nucleic acid. For example, the nucleic acid can comprise DNA, RNA or a chemical analog that binds to the mRNA produced by the target gene. Binding of the antisense nucleic acid prevents translation and thereby inhibits or reduces target protein expression. Antisense nucleic acid molecules may be chemically synthesized using naturally occurring nucleotides or variously modified nucleotides designed to increase the biological stability of the molecules or to increase the physical stability of the duplex formed with mRNA or the native gene e.g., phosphorothioate derivatives and acridine substituted nucleotides. The antisense nucleic acid can be complementary to an entire target gene coding strand, or only to a portion thereof. The antisense sequences may be produced biologically using an expression vector introduced into cells in the form of a recombinant plasmid, phagemid or attenuated virus in which antisense sequences are produced under the control of a high-efficiency regulatory region, the activity of which may be determined by the cell type into which the vector is introduced.

The term "antisense technologies or methods" as used herein refers to technologies and methodologies that use for example, antisense nucleic acids or oligonucleotides; ribozymes or deoxyribozymes, which are catalytically active oligonucleotides that cause RNA cleavage; siRNA nucleic acids and/or shRNA nucleic acids, which employ the RNA interference pathway; to inhibit expression of a target gene. The term "coding region" refers to the region of the nucleotide sequence comprising codons which are translated into amino acid residues.

The term "noncoding region" refers to 5' and 3' sequences which flank the coding region that are not translated into amino acids (i.e., also referred to as 5' and 3' untranslated regions).

The term "siRNA", "siRNA nucleic acid" and/or "siRNA oligonucleotide" refers to a short inhibitory RNA that can be used to reduce or inhibit gene expression of a specific gene by RNA interference (i.e., RNAi). For example, siRNAs can be double-stranded RNA nucleic acids consisting of for example, 21-23 nucleotides that correspond to a target region in a gene of interest (e.g., comprise a sense strand homologous to the target mRNA).

The term "small hairpin RNA", "short hairpin RNA" and/or "shRNA" refers to a short nucleic acid that gives rise to a RNA hairpin that can be used to silence the expression of a target gene via RNA interference. For example, the shRNA comprises a short nucleotide sequence ranging for example from 19-29 nucleotides derived from the target gene, a short spacer, for example, of 4-15 nucleotides (which forms the loop) and a nucleotide sequence that is the reverse complement of the initial target sequence. The shRNA is optionally comprised in a vector that is introduced into cells and utilizes, for example the human H1 RNA or U6 pol III promoters, or other promoter to ensure that the shRNA is always expressed. The vector is usually passed on to daughter cells, allowing the gene silencing to be inherited. For example, in a stable cell, the vector comprising the shRNA is maintained in progeny cells.

The term "RNA interference" as used herein refers to a pathway that can be used to reduce or silence gene expression of a target gene. RNAi activates a cellular degradation pathway directed at mRNAs corresponding (e.g., homologous) to the siRNA or shRNA. Methods of designing specific siRNA and shRNA nucleic acids and administering them are known to a person skilled in the art. It is known in the art that efficient silencing is obtained with siRNA duplex complexes paired to have a two nucleotide 3' overhang. The siRNA or shRNA can also be modified to increase stability. For example, adding two thymidine nucleotides and/or 2'O methylation is thought to add nuclease resistance. A person skilled in the art will recognize that other nucleotides can also be added and other modifications can be made. As another example deoxynucleotide residues (e.g., dT) can be employed to increase stability.

The term "miRNA" refers to microRNAs which are single stranded RNAs, for example, consisting of 22 nucleotides, that are processed from hairpin RNA precursors, for example, about 70 nucleotides long. miRNAs can inhibit gene expression through targeting homologous mRNAs.

The term "morpholino oligonucleotides" refers to an antisense technology used to block access of other molecules to the target mRNA sequence. Morpholino oligonucleotides are short chains of about 25 morpholino subunits. Each subunit is comprised of a nucleic acid base, a 6 membered morpholine ring and a non-ionic phosphorodiamidate intersubunit linkage. Morpholinos block small (~25 base) regions of the base-pairing surfaces of ribonucleic acid (RNA).

As used herein, the terms "peptide nucleic acids" or "PNAs" refer to nucleic acid mimics, e.g., DNA mimics, in which the deoxyribose phosphate backbone is replaced by a pseudopeptide backbone and only the four natural nucleobases are retained. The neutral backbone of PNAs has been shown to allow for specific hybridization to DNA and RNA under conditions of low ionic strength. The synthesis of PNA oligomers can be performed using standard solid phase peptide synthesis protocols as described in Hyrup B. et al. (1996) supra; Perry-O'Keefe et al. Proc. Natl. Acad. Sci. 93: 14670 675.

By "at least moderately stringent hybridization conditions" it is meant that conditions are selected which promote selective hybridization between two complementary nucleic acid molecules in solution. Hybridization may occur to all or a portion of a nucleic acid sequence molecule. The hybridizing portion is typically at least 15 (e.g., 20, 25, 30, 40 or 50)

nucleotides in length. Those skilled in the art will recognize that the stability of a nucleic acid duplex, or hybrids, is determined by the Tm, which in sodium containing buffers is a function of the sodium ion concentration and temperature (Tm=81.5° C.−16.6 (Log 10 [Na+])+0.41(%(G+C)−600/l), or similar equation). Accordingly, the parameters in the wash conditions that determine hybrid stability are sodium ion concentration and temperature. In order to identify molecules that are similar, but not identical, to a known nucleic acid molecule a 1% mismatch may be assumed to result in about a 1° C. decrease in Tm, for example, if nucleic acid molecules are sought that have a >95% identity, the final wash temperature will be reduced by about 5° C. Based on these considerations those skilled in the art will be able to readily select appropriate hybridization conditions. In preferred embodiments, stringent hybridization conditions are selected. By way of example the following conditions may be employed to achieve stringent hybridization: hybridization at 5× sodium chloride/sodium citrate (SSC)/5×Denhardt's solution/1.0% SDS at Tm—5° C. based on the above equation, followed by a wash of 0.2×SSC/0.1% SDS at 60° C. Moderately stringent hybridization conditions include a washing step in 3×SSC at 42° C. It is understood, however, that equivalent stringencies may be achieved using alternative buffers, salts and temperatures. Additional guidance regarding hybridization conditions may be found in: Current Protocols in Molecular Biology, John Wiley & Sons, N.Y., (1989, 2002), and in: Sambrook et al., Molecular Cloning: a Laboratory Manual, Cold Spring Harbor Laboratory Press, (2001).

The term "antibody" as used herein is intended to include monoclonal antibodies, polyclonal antibodies, and chimeric antibodies. The antibody may be from recombinant sources and/or produced in transgenic animals. The term "antibody fragment" as used herein is intended to include Fab, Fab', F(ab')2, scFv, dsFv, ds-scFv, dimers, minibodies, diabodies, and multimers thereof and bispecific antibody fragments. Antibodies can be fragmented using conventional techniques. For example, F(ab')2 fragments can be generated by treating the antibody with pepsin. The resulting F(ab')2 fragment can be treated to reduce disulfide bridges to produce Fab' fragments. Papain digestion can lead to the formation of Fab fragments. Fab, Fab' and F(ab')2, scFv, dsFv, ds-scFv, dimers, minibodies, diabodies, bispecific antibody fragments and other fragments can also be synthesized by recombinant techniques.

The term "peptide mimetics" as used herein refers are structures which serve as substitutes for peptides in interactions between molecules (See Morgan et al. (1989), Ann. Reports Med. Chem. 24:243-252 for a review). Peptide mimetics include synthetic structures which may or may not contain amino acids and/or peptide bonds but retain structural and functional features of a peptide, such as its ability to bind and inhibit the expression or activity of a steroidogenic enzyme of interest. Peptide mimetics also include peptoids, oligopeptides (Simon et al. (1972) Proc. Natl. Acad, Sci USA 89:9367); and peptide libraries.

The term "aptamer" as used herein refers to short strands of nucleic acids that can adopt highly specific 3-dimensional conformations. Aptamers can exhibit high binding affinity and specificity to a target molecule. These properties allow such molecules to specifically inhibit the functional activity of proteins and are included as agents that inhibit, for example, steroidogenesis enzyme such as CYP21A2.

The term "a steroid production profile for an endocrine disruptor" as used herein refers to a plurality of data points each corresponding to a level of steroid produced by a particular modified or unmodified cell in response to a particular endocrine disruptor or a mixture of chemicals under a set of conditions. Which steroids are increased or decreased and to what extent they are increased or decreased, can provide information on which endocrine pathway is affected by a particular endocrine disruptor or putative endocrine disruptor.

The definitions and embodiments described in particular sections are intended to be applicable to other embodiments herein described for which they are suitable as would be understood by a person skilled in the art or unless otherwise stated.

II. Steroidogenesis Modified Cells

Disclosed herein are steroidogenesis modified cells such as steroidogenesis modified H295R cells, which are useful for identifying endocrine disrupting chemicals or endocrine disruptors, for example, using a steroidogenesis modified H295R steroidogenesis assay also disclosed herein. As required by USEPA and OECD, over the next decade thousands of chemicals will have to be screened for their endocrine disrupting properties using EPA's Tier 1 screening battery. The steroidogenesis modified H295R cells and assays disclosed herein will provide a unique and significantly improved screening assay, for example, as a replacement of one of the current Tier 1 tests of EPA's EDSP, and that overcomes some of current uncertainties and limitations of the present H295R Steroidogeneis assay. For example, it has been found that several of the steroidogenesis modified H295R cell lines not only exhibit increased basal estradiol production but also exhibit better stability in terms of hormone production compared to parental H295R cells. It is also demonstrated herein that JEG-3 and R2C exhibit increased basal steroid, production for one or more steroids (e.g. estradiol, and also 17ahydrorxyprogesterone and estone in the case of R2C cells) compared to H295R cells making these cells also useful in the methods disclosed herein. It is predicted that knock down of one or more genes in the steroidogenesis pathway in JEG-3 or R2C cells would similarly produce cells lines with further increases in basal steroid levels.

Accordingly, an aspect of the disclosure provides an isolated steroidogenesis modified cell comprising a steroid biosynthesis knockdown nucleic acid operatively linked to a promoter, wherein the steroid biosynthesis knock down nucleic acid reduces the expression of a steroidogenesis pathway gene, for example a gene selected from desmolase (20,22 Desmolase) (CYP11A1), steroid 17α-hydroxylase (CYP17A1); steroid 21-hydroxylase (CYP21A2); aromatase (CYP19A1); 3β-hydroxysteroid dehydrogenase (3βHSD1 & 3βHSD2); steroid 11β hydroxylase (CYP11B1); aldosterone synthetase (CYP11B2); 17β hydroxysteroid dehydrogenase (17βHSD1); steroidogenic acute regulatory protein (StAR); 3-hydroxy-3-methylglutaryl-coenzyme A reductase (HMGR); 5α-Reductase 2, estrogen-preferring sulfotransferase (SULT1E1); cytochrome P450 family 3 subfamily A polypeptide 4 (CYP3A4); and UDP-glucuronosyltransferase (UGT1A1). Examples of NCBI Entrez Gene ID for each of these genes is provided in Table 1, and the corresponding genomic, mRNA and protein sequences are herein incorporated by reference.

In an embodiment, the isolated modified steroidogenesis cell is an isolated modified H295R cell comprising a steroid biosynthesis knockdown nucleic acid operatively linked to a promoter, wherein the steroid biosynthesis knock down nucleic acid reduces the expression of a gene selected from CYP11A1, CYP17A1, CYP21A2, CYP19A1, 3βHSD1 &

3βHSD2, CYP11B1, CYP11B2, 17βHSD1, StAR, HMGR, 5α-Reductase 2, SULT1E1, CYP3A4 and UGT1A1.

As H295R cells are a strain of H295 cells, person skilled in the art would recognize that parental H295 cells and other strains thereof can also be used to make steroidogenesis modified H295 cells. Accordingly, in an embodiment, the disclosure provides an isolated steroidogenesis modified H295 cell comprising a steroid biosynthesis knockdown nucleic acid operatively linked to a promoter, wherein the steroid biosynthesis knock down nucleic acid reduces the expression of a gene selected from CYP11A1, CYP17A1, CYP21A2, CYP19A1, 3βHSD1 & 3βHSD2, CYP11B1, CYP11B2, 17βHSD1, StAR, HMGR, 5α-Reductase 2, SULT1E1, CYP3A4 and UGT1A1.

Similarly, other cells such as other undifferentiated fetal adrenal cell lines with similar properties to H295R cells that produce steroid hormones, for example which produce sex hormones namely androgens and estrogens, can similarly be manipulated to knock down expression of a steroidogenesis gene to increase expression of for example estradiol (E2), and are useful in methods described herein. Examples include JEG-3 cells and R2C cells.

Accordingly, in another embodiment, the isolated modified steroidogenesis cell is an isolated modified JEG-3 cell. In a further embodiment, the isolated modified steroidogenesis cell is an isolated modified R2C cell.

In an embodiment, the isolated cell is a stable cell line. In a further embodiment, the steroid biosynthesis knock down nucleic acid comprises a siRNA nucleic acid, a shRNA nucleic acid or an antisense nucleic acid. Antisense technologies such as siRNA, shRNA and antisense nucleic acids are well known in the art and are further described below.

The steroidogenesis modified cell, for example the steroidogenesis modified H295R cell, can also comprise combinations of knocked down steroidogenesis genes. Accordingly, in an embodiment, the isolated modified steroidogenesis cell comprises knock down of one or more genes selected from CYP11A1, CYP17A1, CYP21A2, CYP19A1, 3βHSD1 & 3βHSD2, CYP11B1, CYP11B2, 17βHSD1, StAR, HMGR, 5α-Reductase 2, SULT1E1, CYP3A4 and UGT1A1. In an embodiment, the steroid biosynthesis nucleic acid comprises In an embodiment, the cell comprises, at least two steroid biosynthesis knockdown nucleic acids operatively linked to a promoter, wherein each steroid biosynthesis knock down nucleic acid reduces the expression of a gene selected from the group CYP21A2, CYP11A1, CYP17A1, CYP19A1, 3-βHSD1, 3-βHSD2, 17-βHSD1, StAR, HMGR, CYP11B2, CYP11B1, 5α-Reductase 2, SULT1E1, CYP3A4 and UGT1A1. In a further embodiment, the cell comprises at least three or at least four steroid biosynthesis knockdown nucleic acids, operatively linked to a promoter. For example, a bicistronic vector can be used to knock down the expression of two genes, or two vectors can be employed. Further, a single promoter is useful to drive expression of multiple constructs. Alternatively, each or a subset of constructs, e.g. each shRNA nucleic acid, can be driven by a dedicated promoter. For example, each steroid biosynthesis knock down nucleic acid can be operatively linked to a separate promoter, and/or a single promoter can be operatively linked to two or more steroid biosynthesis knock down nucleic acids.

a) CYP21A2 Modified Cells

The steroidogenic properties of the H295R cell line have been intensively investigated and the CYP21A gene was identified to be one of the key factors that could alter the production of steroid sex hormones by these cells. A commercially available RNAi technique was applied to genetically knockdown the CYP21A gene in the parent H295R cell, and thus, successfully generate a novel stable cell line. This new CYP21A knockdown H295R cell line carries a favourable characteristic in that the basal 17β-estradiol production was increased from approximately 10-50 to 400 pg/ml. As a consequence, basal 17β-estradiol levels in the stable CYP21A knockdown H295R cell line is 200-times greater than the detection limit of current technologies, which significantly increases the sensitivity over the current H295R steroidogenesis assay. Basal levels of 17β-estradiol are increased almost 10 fold in JEG-3 cells and about 61 fold in R2C cells compared to H295R cells and it is expected that modification of steroidogenesis pathway genes would further increase the levels of some steroids, for example 17β-estradiol.[

Accordingly, in an embodiment of the disclosure, the one or more genes for which expression is reduced comprises CYP21A2. In another embodiment, the one or more genes is CYP21A2. In an embodiment, the steroidogenesis modified cell comprises a CYP21A2 knockdown H295R cell (e.g. H295R/CYP21A2) wherein the steroid biosynthesis knockdown nucleic acid reduces the expression of CYP21A2. For modified cells wherein the expression of CYP21A2 is reduced, the steroid biosynthesis knock down nucleic acid comprises a nucleic acid that targets the CYP21A2 to reduce its expression (i.e. a CYP21A2 knock down nucleic acid). For example, a siRNA, shRNA or antisense nucleic acid that is specific for CYP21A2 can be used as a CYP21A2 knock down nucleic acid. In an embodiment, the CYP21A2 knock down nucleic acid comprises CCGGCGACAACTTAATGC-CTGCCTACTCGAGTAGGCAGGCATTAAGTTGTC GTTTTTG (SEQ ID NO:1).

In an embodiment, the disclosure provides an isolated steroidogenesis modified H295R cell comprising a CYP21A2 knockdown nucleic acid operatively linked to a promoter, wherein the CYP21A2-specific knock down nucleic acid reduces the expression of CYP21A2, but not other genes.

b) Knockdown of Other Steroidogenesis Pathway Enzymes

Steroidogenesis modified cells comprising reduced or knockdown expression of other enzymes involved in steroidogenesis are also herein provided. Such modified cells are in certain embodiments alternatives, and/or are employed in addition, to CYP21A2 in the steroidogenesis assays, and include the alteration of CYP11B1 and 2 to achieve a partial or complete suppression of the corticoid synthesis pathways. In addition to the alteration of sex steroid synthesis, effects on corticoid synthesis such as cortisol or aldosterone are increasingly of concern in context with the phenomenon of endocrine disruption. Therefore, steroidogeneisis modified knockdown cells of steroid biosynthesis genes that are expected to affect mineralo- and/or gluco-corticoid synthesis pathways, for example due to—but not limited to—alteration of the expression of CYP17, CYP21, and CYP11B1 and 2 can be usefully exploited in steroidogenesis assays to assess the effect of a test substance on corticoid synthesis.

Accordingly, in an embodiment of the disclosure, the one or more genes which expression of is reduced comprises CYP11A1. In another embodiment, the one or more genes is CYP11A1. In an embodiment, the steroidogenesis modified cell comprises a CYP11A1 knockdown cell (e.g., H295R/CYP11A1), wherein the steroid biosynthesis knockdown nucleic acid reduces the expression of CYP11A1. In an embodiment, the steroidogenesis modified H295R cell comprises a CYP11A1 knockdown cell (i.e. H295R/CYP11A1), wherein the steroid biosynthesis knockdown nucleic acid reduces the expression of CYP11A1. For modified cells wherein the expression of CYP11A1 is reduced, the steroid biosynthesis knock down nucleic acid comprises a nucleic acid that targets the CYP11A1 to reduce its expression (i.e., a CYP11A1 knock down nucleic acid). For example, a siRNA, shRNA or antisense nucleic acid that is specific for CYP11A1 can be used as a CYP11A1 knock down nucleic acid. In an embodiment, the knock down nucleic acid comprises TGCTGTTGACAGTGAGCGACCTGCA-GAGATATCTTGTAAATAGTGAAGCCA CAGATGTATTTACAAGATATCTCTGCAGGGTGCCTACTGCCTCGGA (SEQ ID NO:2).

In another embodiment, the one or more genes comprises CYP17A1. In another embodiment, the one or more genes is CYP17A1. In a further embodiment, the steroidogenesis modified H295R cell comprises a CYP17A1 knockdown cell (i.e., H295R/CYP17A1), wherein the steroid biosynthesis knock down nucleic acid comprises TGCTGTTGACAGTGAGCGCGGGCACAGAAGTTATCATCAAT-AGTGAAGCCA CAGATGTATTGATGATAACTTCTGTGCCCTTGCCTACTGCCTCGGA (SEQ ID NO:3).

In another embodiment, the one or more genes comprises CYP19A1. In another embodiment, the one or more genes is CYP19A1. In an embodiment, the steroidogenesis modified cell comprises a CYP19A1 knockdown cell (e.g., H295R/CYP19A1), wherein the steroid biosynthesis knockdown nucleic acid reduces the expression of CYP19A1. In a further embodiment, the steroidogenesis modified H295R cell comprises a CYP19A1 knockdown cell (i.e., H295R/CYP19A1), wherein the steroid biosynthesis knock down nucleic acid comprises TGCTGTTGACAGTGAGCGAAGAACCAG-GCTACAAGAGAAATAGTGAAGCCA CAGATGTATTTCTCTTGTAGCCTGGTTCTCTGCCTACTGCCTCGGA (SEQ ID NO:4).

In another embodiment, the one or more genes comprises 3-βHSD1. In a further embodiment, the one or more genes is 3-βHSD1. In an embodiment, the steroidogenesis modified cell comprises a 3-βHSD1 knockdown cell (e.g., H295R/3-βHSD1), wherein the steroid biosynthesis knockdown nucleic acid reduces the expression of 3-βHSD1. In yet a further embodiment, the steroidogenesis modified H295R cell comprises a 3-βHSD1 knockdown cell (i.e., H295R/3-βHSD1), wherein the steroid biosynthesis knock down nucleic acid comprises CCGGCGCCTGTATCATTGATGTCTTCTCGAGAAGACATCAATGATACAGGC GTTTTTG (SEQ ID NO:5).

In a further embodiment, the one or more genes comprises 3-βHSD2. In another embodiment, the one or more genes is 3-βHSD2. In an embodiment, the steroidogenesis modified cell comprises a 3-Bhsd2 knockdown cell (e.g., H295R/3-Bhsd2), wherein the steroid biosynthesis knockdown nucleic acid reduces the expression of 3-Bhsd2. In yet another embodiment, the steroidogenesis modified H295R cell comprises a 3-βHSD2 knockdown cell (i.e., H295R/3-βHSD2), wherein the steroid biosynthesis knock down nucleic acid comprises TGCTGTTGACAGTGAGCGACCACACAGT-CACATTATCAAATAGTGAAGCCA CAGATGTATTTGATAATGTGACTGTGTGGCTGCCTACTGCCTCGGA (SEQ ID NO:6).

In another embodiment, the one or more genes comprises 17-βHSD1. In another embodiment, the one or more genes is 17-βHSD1. In an embodiment, the steroidogenesis modified cell comprises a 17-βHSD1 knockdown cell (e.g., H295R/17-βHSD1), wherein the steroid biosynthesis knockdown nucleic acid reduces the expression of 17-βHSD1. In a further embodiment, the steroidogenesis modified H295R cell comprises a 17-βHSD1 knockdown cell (i.e., H295R/17-βHSD1), wherein the steroid biosynthesis knock down nucleic acid comprises TGCTGTTGACAGTGAGCGCGGGTGGCTAATTAAGATAGATT-AGTGAAGCCA CAGATGTAATCTATCTTAATTAGC-CACCCATGCCTACTGCCTCGGA (SEQ ID NO:7).

In yet another embodiment, the one or more genes comprises StAR. In another embodiment, the one or more genes is StAR. In an embodiment, the steroidogenesis modified cell comprises a StAR knockdown cell (e.g., H295R/StAR), wherein the steroid biosynthesis knockdown nucleic acid reduces the expression of StAR. In yet a further embodiment, the steroidogenesis modified H295R cell comprises a StAR knockdown cell (i.e., H295R/StAR), wherein the steroid biosynthesis knock down nucleic acid comprises CCGGGCT-GCCCAAGAGCATCATCAACTCGAGT-TGATGATGCTCTTGGGCA GCTTTTTG (SEQ ID NO:8).

In another embodiment, the one or more genes comprises HMGR. In another embodiment, the one or more genes is HMGR. In an embodiment, the steroidogenesis modified cell comprises a HMGR knockdown cell (e.g., H295R/HMGR), wherein the steroid biosynthesis knockdown nucleic acid reduces the expression of HMGR. In yet a further embodiment, the steroidogenesis modified H295R cell comprises a HMGR knockdown cell (i.e., H295R/HMGR) wherein the steroid biosynthesis knock down nucleic acid comprises CCGGGCAGTGATAAAGGAGGCATTTCTC-GAGAAATGCCTCCTTTATCACTG CTTTTTG (SEQ ID NO:9).

In another embodiment, the one or more genes comprises CYP11B2. In another embodiment wherein the one or more genes is CYP11B2. In an embodiment, the steroidogenesis modified cell comprises a CYP11B2 knockdown cell (e.g., H295R/CYP11B2), wherein the steroid biosynthesis knockdown nucleic acid reduces the expression of CYP11B2. In yet a further embodiment, the steroidogenesis modified H295R cell comprises a CYP11B2 knockdown cell (i.e., H295R/CYP11B2) wherein the steroid biosynthesis knock down nucleic acid comprises CCGGCCTCACTTTCAGAGCGAT-TAACTCGAGTTAATCGCTCTGAAAGTGAG GTTTTTG (SEQ ID NO:10).

In another embodiment, the one or more genes comprises CYP11B1. In a further embodiment, the one or more genes is CYP11B1. In an embodiment, the steroidogenesis modified cell comprises a CYP11B1 knockdown cell (e.g., H295R/CYP11B1), wherein the steroid biosynthesis knockdown nucleic acid reduces the expression of CYP11B1. In yet a further embodiment, the steroidogenesis modified H295R cell comprises a CYP11B1 knockdown cell (i.e., H295R/CYP11B1), wherein the steroid biosynthesis knock down nucleic acid comprises CCGGCCCTCAACAGTACAC-CAGCATCTCGAGATGCTGGTGTACTGTTGAGG GTTTTTG (SEQ ID NO: 11).

In yet another embodiment, the one or more genes comprises 5α-Reductase 2. In another embodiment, the one or more genes is 5α-Reductase 2. In an embodiment, the steroidogenesis modified cell comprises a 5α-Reductase 2 knockdown cell (e.g., H295R/5α-Reductase 2), wherein the steroid biosynthesis knockdown nucleic acid reduces the expression of 5α-Reductase 2. In a further embodiment, the steroidogenesis modified H295R cell comprises a 5α-Reductase 2 knock down cell (i.e., H295R/5α-Reductase 2), wherein the steroid biosynthesis knock down nucleic acid comprises CCGGCCTCAAGATGTTTGAGGACTACTC-GAGTAGTCCTCAAACATCTTGAG GTTTTTG (SEQ ID NO:12).

In another embodiment, one or more genes comprises SULT1E1. In another embodiment, the one or more genes is SULT1E1. In an embodiment, the steroidogenesis modified cell comprises a SULT1E1 knockdown cell (e.g., H295R/

SULT1E1), wherein the steroid biosynthesis knockdown nucleic acid reduces the expression of SULT1E1. In a further embodiment, the steroidogenesis modified H295R cell comprises a SULT1E1. knockdown cell (i.e., H295R/SULT1E1.), wherein the steroid biosynthesis knock down nucleic acid comprises CCGGCCAGAAATTGTCGCCCTTCATCTC-GAGATGAAGGGCGACAATTTCTG GTTTTTG (SEQ ID NO:13).

In another embodiment, one or more genes comprises CYP3A4. In another embodiment, the one or more genes is CYP3A4. In an embodiment, the steroidogenesis modified cell comprises a CYP3A4 knockdown cell (e.g., H295R/CYP3A4), wherein the steroid biosynthesis knockdown nucleic acid reduces the expression of CYP3A4. In a further embodiment, the steroidogenesis modified H295R cell comprises a CYP3A4 knockdown cell (i.e., H295R/CYP3A4), wherein the steroid biosynthesis knock down nucleic acid comprises CCGGCCTTACATATACACACCCTTTCTC-GAGAAAGGGTGTGTATATGTAAG GTTTTTG (SEQ ID NO:14).

In another embodiment, one or more genes comprises UGT1A1. In another embodiment, the one or more genes is UGT1A1. In an embodiment, the steroidogenesis modified cell comprises a UGT1A1 knockdown cell (e.g., H295R/UGT1A1), wherein the steroid biosynthesis knockdown nucleic acid reduces the expression of UGT1A1. In a further embodiment, the steroidogenesis modified H295R cell comprises a UGT1A1 knockdown cell (i.e., H295R/UGT1A1.), wherein the steroid biosynthesis knock down nucleic acid comprises CCGGCCCACTGTATTCTTCTTGCATCTC-GAGATGCAAGAAGAATACAGTGG GTTTTTG (SEQ ID NO: 15).

Gene Knock Down Levels and Hormone Levels

The expression level of one or more steroidogenesis genes e.g., genes for one or more enzymes involved in steroidogenesis, is decreased in the modified cells described herein.

In an embodiment, the modified cell expresses at least 10%, at least 15%, at least 20%, at least 25%, at least 30%, at least 35%, at least 40%, at least 45%, at least 50% at least 55%, at least 60%, at least 65%, at least 70%, at least 80%, at least 85%, or at least 90% less of the one or more genes (e.g. mRNA or protein) compared to a control, assessed for example by determining the level of expressed mRNA or protein and/or enzyme activity. In an embodiment, the control is unmodified H295R cells.

In another embodiment, the cell produces an increased level of at least one steroid or steroid precursor. The increased level is, in an embodiment, an increased concentration of the steroid or steroid precursor.

In an embodiment, the at least one steroid is a sex steroid. In another embodiment, the modified cell produces an increased level of androstenedione (AD), testosterone (T), dihydrotestosterone (DHT), estrone (E1) and/or 17β estradiol (E2).

In another embodiment, the steroid is a corticosteroid. In a further embodiment the corticosteroid is a mineralocorticosteroid or a glucocorticosteroid. In another embodiment, the steroid is cortisol and/or aldosterone.

In another embodiment, the cell produces at least 10%, at least 15%, at least 20%, at least 25%, at least 30%, at least 35%, at least 40%, at least 45%, at least 50% at least 55%, at least 60%, at least 65%, at least 70%, at least 80%, at least 85%, at least 90%, or more of the at least one steroid. In a further embodiment, the cell produces at least 1×, at least 2×, at least 3×, at least 4×, at least 5×, at least 6×, at least 7×, at least 8×, at least 9×, at least 10×, at least 11×, at least 12×, at least 15×, at least 20×, at least 25×, at least 30×, at least 40×, at least 50×, at least 60×, at least 70×, at least 80×, at least 90×, at least 100×, at least 125×, at least 150×, at least 175×, at least 200× or more of the at least one steroid.

Hormone production is typically a function of time which differs greatly among hormones. For example, E2 production can be less than 100 pg/mL/48 h (e.g. per 200,000-300,000 cells) while concentrations of androstenedione can be around 100 ng/mL/48 h (e.g. per 200,000-300,000 cells), and some of the corticosteroids can even be produced at greater concentrations. In an embodiment, the steroidogenesis modified cells produce at least 10 pg/ml, least 20 pg/ml, at least 30 pg/ml, at least 40 pg/ml, at least 50 pg/ml at least 60 pg/ml, at least 70 pg/ml, at least 80 pg/ml, at least 90 pg/ml, at least 100 pg/ml, at least 125 pg/ml, at least 150 pg/ml, at least 175 pg/ml, at least 200 pg/ml, at least 250 pg/ml, at least 300 pg/ml, at least 350 pg/ml, at least 400 pg/ml, at least 500 pg/ml, at least 600 pg/ml, at least 800 pg/ml, or at least 1,000 pg/ml of 17beta-estradiol.

In a further embodiment, the cell produces at least 1 attog/cell per 48 hrs, at least 3 attog/cell per 48 hrs, at least 10 attog/cell per 48 hrs, at least 20 attog/cell per 48 hrs, at least 30 attog/cell per 48 hrs, at least 40 attog/cell per 48 hrs, at least 50 attog/cell per 48 hrs, at least 60 attog/cell per 48 hrs, at least 70 attog/cell per 48 hrs, at least 80 attog/cell per 48 hrs, at least 90 attog/cell per 48 hrs, at least 100 attog/cell per 48 hrs, at least 125 attog/cell per 48 hrs, at least 150 attog/cell per 48 hrs, at least 175 attog/cell per 48 hrs, at least 200 attog/cell per 48 hrs, at least 250 attog/cell per 48 hrs, at least 300 attog/cell per 48 hrs, or at least 400 attog/cell per 48 hrs or at least 800 attog/cell per 48 hrs of the at least one steroid. In another embodiment, the cell produces at least 1 femtog/cell/48 h, at least 3 femtog/cell/48 h, at least 5 femtog/cell/48 h, at least 10 femtog/cell/48 h, at least 20 femtog/cell/48 h, at least 30 femtog/cell/48 h, at least 40 femtog/cell/48 h, at least 50 femtog/cell/48 h, at least 60 femtog/cell/48 h, at least 70 femtog/cell/48 h, at least 80 femtog/cell/48 h, at least 90 femtog/cell/48 h, at least 100 femtog/cell/48 h, at least 125 femtog/cell/48 h, at least 150 femtog/cell/48 h, at least 175 femtog/cell/48 h, at least 200 femtog/cell/48 h, at least 250 femtog/cell/48 h, at least 300 femtog/cell/48 h, at least 400 femtog/cell/48 h, at least 800 femtog/cell/48 h, or at least 1,000 femtog/cell/48 h of at least one steroid.

In an embodiment, the cells produces at least 1 attog/cell per 48 hrs, at least 3 attog/cell per 48 hrs, at least 10 attog/cell per 48 hrs, at least 20 attog/cell per 48 hrs, at least 30 attog/cell per 48 hrs, or at least 100 attog/cell per 48 hrs of E2. In another embodiment, the cell produces at least 1 femtog/cell/48 h, at least 3 femtog/cell/48 h, at least 5 femtog/cell/48 h, at least 10 femtog/cell/48 h, at least 20 femtog/cell/48 h, at least 30 femtog/cell/48 h, at least 40 femtog/cell/48 h or at least 200 femtog/cell/48 h of testosterone. In another embodiment, the cell produces at between about 10 femtog/cell/48 h and about 500 femtog/cell/48 h of androstenedione. In another embodiment, the cell produces at between about 1 femtog/cell/48 h and about 100 femtog/cell/48 h of estrone.

In another embodiment, the modified cell further comprises an antibiotic resistance gene nucleic acid operatively linked to a promoter. In an embodiment, the cell is resistant to the antibiotic puromycin. In addition to puromycin acetyltransferase, other antibiotic selection markers include without limitation genes that encode the protein neomycin phosphotransferase and hygromycin B phosphotransferase.

Delivery Vectors

It will be appreciated by one skilled in the art that a variety of delivery vectors and expression vehicles are usefully employed to introduce the nucleic acids described herein into a cell. Vectors that are useful comprise lentiviruses, oncoretroviruses, expression plasmids, adenovirus, and adeno-associated virus. The commonly used shRNA delivery vectors are plasmids, retroviral and lentiviral vectors.

The shRNA nucleic acid introduced into the H295R cell and described in Example 2 comprised in a pLKO.1 plasmid (Thermo Scientific Open Biosystems). As a person skilled in the art would understand, other vectors such as other stably integrating vectors, can also be used. For example, lentiviral vectors suitable for shRNA technologies include vectors available for example, from Thermo Scientific Open Biosystems, Santa Cruz Biotechnology, Inc (www.scbt.com), Ambion (www.ambion.com), Invitrogen (www.invitrogen.com) and Signosis BioSignal Capture (www.signosisinc.com).

The antisense and/or shRNA nucleic acid is in an embodiment, operatively linked to a promoter. Any promoter that provides sufficient expression of the antisense or shRNA molecule to knock down expression of the target gene can be used. Suitable promoters include for example, human H1 RNA promoter, human U6 promoter, human phosphoglycerate kinase promoter (hPGK) SV40, and CMV early enhancer/chicken β actin (CAG) promoter.

As other methods can be used to knock down expression of a target gene, in an embodiment, the disclosure provides an isolated steroidogenesis modified cell, for example an isolated steroidogenesis modified H295R cell, comprising a steroid biosynthesis knock down agent, wherein the steroid biosynthesis knock down agent reduces the expression of a gene selected from CYP21A2, CYP11A1, CYP17A1, CYP19A1, 3-βHSD1, 3-βHSD2, 17-βHSD1, StAR, HMGR, CYP11B2, CYP11B1, 5α-Reductase 2, SULT1E1, CYP3A4 and UTG1A1.

III. Methods i) Method of Producing Cell Lines

The disclosure provides a method of making an isolated steroidogenesis modified cell such an isolated steroidogenesis modified H295R or H295 cell comprising a steroid biosynthesis knock down nucleic acid operatively linked to a promoter, wherein the steroid biosynthesis knockdown nucleic acid reduces the expression of a gene selected from the group CYP21A2, CYP11A1, CYP17A1, CYP19A1, 3-βHSD1, 3-βHSD2, 17-βHSD1, StAR, HMGR, CYP11B2, CYP11B1, 5α-Reductase 2, SULT1E1, CYP3A4 and UGT1A1.

Accordingly, another aspect provides a method of making a steroid-biosynthesis-modified-cell, in an embodiment, a steroid-biosynthesis-modified H295R or a steroid-biosynthesis-modified H295 cell comprising introducing a steroid biosynthesis knock down nucleic acid operatively linked to a promoter into a steroidogenesis cell (e.g. a H295R, H295, JEG-3 or RC2 cell), and selecting cells wherein the steroid biosynthesis knock down nucleic acid reduces the expression of a gene selected from the group CYP21A2, CYP11A1, CYP17A1, CYP19A1, 3-βHSD1, 3-βHSD2, 17-βHSD1, StAR, HMGR, CYP11B2, CYP11B1, 5α-Reductase 2, SULT1E1, CYP3A4 and UGT1A1.

A number of technologies can be used to make the isolated cells described herein. Recombinant and antisense technologies can be used to make the steroidogenesis modified cells (such as the steroidogenesis modified H295R and/or H295 cells) by introducing a nucleic acid specific for the gene to be knocked down. In an embodiment, the steroid biosynthesis knock down nucleic acid comprises a siRNA nucleic acid, a shRNA nucleic acid or an antisense nucleic acid. In another embodiment, zinc finger proteins are used to knock down expression the desired gene. Chemical inhibition and chemical mutagenesis methods can also be used in other embodiments. Other methods that knockdown or knockout expression of the desired gene are also suitable.

Accordingly in an embodiment, the disclosure provides a method of making an isolated steroidogenesis modified cell comprising introducing a steroid biosynthesis knock down agent, and selecting cells wherein the steroid biosynthesis knock down agent reduces the expression of a gene selected from CYP21A2, CYP11A1, CYP17A1, CYP19A1, 3-βHSD1, 3-βHSD2, 17-βHSD1, StAR, HMGR, CYP11B2, CYP11B1, 5α-Reductase 2, SULT1E1, CYP3A4 and UTG1A1. In an embodiment the isolated steroidogenesis modified cell is a isolated steroidogenesis modified H295R cell.

A number of siRNA, shRNA and antisense nucleic acids are suitable for making the cells disclosed herein. In an embodiment, the siRNA nucleic acid (each strand) is between 20 and 30, 31 and 40, 41 and 50 residues long. In an embodiment the siRNA (each strand) is 20, 21, 22, 23, 24 or 25 residues long. In another embodiment, the shRNA comprises a hairpin loop and is between 40 and 80 residues long. In an embodiment, the shRNA comprises a hairpin loop and is 40, 41, 42, 43, 44, 45, or 46 residues long.

In an embodiment, the shRNA nucleic acid comprises a sequence listed in Table 2.

The steroid biosynthesis knock down nucleic acid for example, a shRNA, siRNA or antisense nucleic acid, can be comprised in a vector that is maintained in the modified cell, for example, by stable integration. In an embodiment, the siRNA, shRNA and/or antisense nucleic acid is comprised in a vector. A retroviral vector is suitable for stably integrating a shRNA, siRNA or antisense nucleic acid comprised therein. Accordingly in an embodiment, the steroid biosynthesis knock down nucleic acid operatively linked to a promoter is comprised in a lentiviral plasmid construct. Other suitable vectors are described herein.

In an embodiment, a selection marker nucleic acid operatively linked to a promoter is also introduced, optionally wherein the selection marker nucleic acid encodes an antibiotic resistance gene and the cell is selected by antibiotic selection. In an embodiment, the cell is selected with puromycin using known selection techniques.

The nucleic acid molecules described herein, can be constructed using chemical synthesis and enzymatic ligation reactions using procedures known in the art. For example, an antisense nucleic acid (e.g., an antisense oligonucleotide) or a siRNA oligonucleotide can be chemically synthesized using naturally occurring nucleotides or variously modified nucleotides designed to increase the biological stability of the molecules or to increase the physical stability of the duplex formed between the hybridizing strands, e.g., phosphorothioate derivatives and acridine substituted nucleotides can be used. Examples of modified nucleotides which can be used to generate the antisense nucleic acid include 5-fluorouracil, 5-bromouracil, 5-chlorouracil, 5-iodouracil, hypoxanthine, xantine, 4-acetylcytosine, 5-(carboxyhydroxylmethyl)uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl)uracil, (acp3)w, and 2,6-diaminopurine. Alternatively, the nucleic acid molecules can be produced biologically using an expression vector into which a nucleic acid has been subcloned in an antisense orientation (e.g., RNA transcribed from the inserted nucleic acid will be of an antisense orientation to a target nucleic acid of interest, or in the case of shRNA, the RNA transcribed will be in a short hairpin orientation corresponding to a target nucleic acid of interest).

Other oligonucleotides may contain nucleotides containing polymer backbones, cyclic backbones, or acyclic backbones. For example, the nucleotides may have morpholino backbone structures (U.S. Pat. No. 5,034,506). Oligonucleotides may also contain groups such as reporter groups, a group for improving the pharmacokinetic properties of an oligonucleotide, and/or a group for improving the pharmacodynamic properties of an oligonucleotide. Oligonucleotides may also have sugar mimetics.

The siRNA, shRNA or antisense nucleic acids can target a coding region of the target gene or a non-coding region of the target gene. For example, gene expression can be inhibited by targeting nucleotide sequences complementary to the regulatory region of the target gene (e.g., promoters and/or enhancers) to form triple helical structures that prevent transcription of the target gene. See generally, Helene, C. (1991) Anticancer Drug Des. 6(6):569 84; Helene, C. et al. (1992) Ann. N.Y. Acad. Sci. 660:27 36; and Maher, L. J. (1992) Bioassays 14(12):807 15.

The nucleic acids disclosed herein can be modified at the base moiety, sugar moiety or phosphate backbone to improve, e.g., the stability, hybridization, or solubility of the molecule. For example, the deoxyribose phosphate backbone of the nucleic acid molecules can be modified to generate peptide nucleic acids (see Hyrup B. et al. (1996) Bioorganic & Medicinal Chemistry 4 (1): 5 23).

In an embodiment, the nucleic acid molecule is a PNA. The neutral backbone of PNAs has been shown to allow for specific hybridization to DNA and RNA under conditions of low ionic strength. The synthesis of PNA oligomers can be performed using standard solid phase peptide synthesis protocols as described in Hyrup B. et al. (1996) supra; Perry-O'Keefe et al. Proc. Natl. Acad. Sci. 93: 14670 675.

ii) Assays For Identifying Endocrine Disrupting Chemicals (EDC) Using Steroidogenesis Modified Cells Such as Steroidogenesis Modified H295R and/or Steroidogenesis Modified H295 Cells—Modified Steroidogenesis Assay In response to emerging concerns that substances may alter the function of endocrine systems and result in adverse effects to human health, the U.S. Congress included a provision in the Food Quality Protection Act of 1996 adding section 408 to the Federal Food Drug and Cosmetic Act (FFDCA). This section of the FFDCA requires EPA to:

. . . develop a screening program, using appropriate validated test systems and other scientifically relevant information, to determine whether certain substances may have an effect in humans that is similar to an effect produced by a naturally occurring estrogen, or other such endocrine effect as the Administrator may designate [21 U.S.C. 346 (p)]

In fulfillment of these requirements EPA has been developing and validating in vitro and in vivo assays to determine the potential of chemicals to interact with the endocrine systems and related functions in humans and wildlife. The EPA is recommending a two-tiered approach in the evaluation process. The Tier 1 Screening battery of assays is based on EPA's Endocrine Disruptor Screening and Testing Advisory Committee (EDSTAC) recommendations and aims to identify chemicals affecting the estrogen, androgen & thyroid hormone systems. Tier 2 testing is intended to confirm, characterize and quantify those effects for estrogen, androgen and thyroid active chemicals.

Included in the Tier 1 Screening battery is the H295R Steroidogenesis Assay using the H295R human adrenocortical carcinoma cell line (http://www.epa.gov/endo/pubs/assayvalidation/status.htm). EPA's Endocrine Receptor Screening Program (EDSP) has included this cell-based assay in their Tier 1 Screening battery programs. Furthermore, the H295R Steroidogenesis Assay is currently in the last validation phase of the Test Method Validation Program for the Organization for Economic Cooperation & Development (OECD), which will ultimately result in the development of an OECD Test Guideline for assessing the potential of chemicals to affect steroid hormone synthesis (OECD 2002).

EPA published in the Federal Register a list of pesticide active ingredients and HPV/pesticide inert chemicals selected for initial Tier 1 screening. This initial list for testing was prioritized from a universe of 87,000 chemicals included on the TSCA Inventory, active pesticide ingredients, and ingredients in cosmetics and food additives.

In present disclosure, several stable modified steroidogenesis cell lines were developed including a CYP21A knockdown H295R cell line, a CYP17A1 knockdown H295R cell line and a CYP19A1 knockdown H295R cell line. It is demonstrated herein for example that the CYP21A knockdown H295R cell line overcomes some of the issues associated with the original H295R Steroidogenesis Assay, namely low basal hormone production of estradiol and significantly improved sensitivity now permitting to also identify weak inhibitors of this hormone's production while the properties of the cells to detect inducers of 17β-estradiol and testosterone remain unchanged. Therefore, an increase at the basal production level of 17β-estradiol will significantly improve the sensitivity of this assay, and will help overcoming its current limitations with regard to the identification of inhibitors of different strength.

The stable CYP21A knockdown H295R cell line has herein been developed as a significantly improved screening assay for endocrine disrupting chemicals. A genetic alteration was introduced into the genome of the parent H295R cell line. This modification significantly increased the basal production of testosterone and 17β-estradiol, but without altering the structure of the endogenous steroidogenesis pathway. These novel steroid-producing properties, render this new H295R/CYP21 knock down cell a superior screening tool that outperforms the original assay, making it the preferable assay for its application as part of the EDSP and other national and/or international screening programs.

Accordingly, in another aspect, the disclosure provides a screening assay for identifying an endocrine disruptor comprising:

a) contacting a steroidogenesis cell for example a steroidogenesis modified H295R or H295 cell disclosed herein with a test substance, e.g. a putative EDC;

b) determining a level of at least one steroid or steroidogenic gene expression product (e.g. mRNA or protein concentration) or enzyme activity;

wherein a modulation in the level of the at least one steroid or steroidogenic gene expression product or enzyme activity compared to a control is indicative that the test substance is an endocrine disruptor.

In an embodiment, the steroidogenesis cell is a JEG-3 cell or a steroidogenesis modified JEG-3 cell. In an embodiment, the steroidogenesis cells is a RC2 cell or a steroidogenesis modified RC-2 cell.

In an embodiment, the level of the at least one steroid detected is steroid released by the cell into the culture medium. In another embodiment, the level of the at least one steroid detected is a steroid that is intracellular. In an embodiment, the level of the at least one steroidogenic gene expression product (e.g. mRNA or protein concentration) or enzyme activity is an intracellular level.

The test substance can be any chemical or substance that putatively affects an endocrine system of a vertebrate or invertebrate (e.g. a putative EDC). In an embodiment, the test substance is selected from industrial chemicals, pharmaceuticals, herbicides, fungicides, polycarbonate plastic monomers, agricultural chemicals, antineoplastic agents, contraceptives postcoitals, synthetics, drugs, therapeutic agents, polyvinyl additives, organophosphorus insecticides, peptide hormones, excipients, pharmaceutical aids, spermaticides, preservatives in food, cosmetics, toiletries and pharmaceuticals, and pesticide synergists. Examples of each category are listed in Table 3. The "effect type" as assessed in a steroidogenesis assay using for example H295R cells (e.g. parental or unmodified cells) is provided in Table 3.

A significant proportion of the substances listed in Table 3 are categorized as weak effectors or negatives using H295R cells. Accordingly, in an aspect of the disclosure, the herein described steroidogenesis modified H295R cells provide a significantly improved screening tool that eliminates uncertainty associated with the below listed assessment of chemicals.

In an embodiment, the at least one steroid is a sex steroid. In an embodiment, at least one steroid is selected from androstenedione, testosterone, dihydrotestosterone, estrone and E2.

In another embodiment, the steroid is a corticosteroid. In a further embodiment, the corticosteroid is a mineralocorticosteroid or a glucocorticosteroid. In another embodiment, the steroid is cortisol or aldosterone.

In another embodiment, the at least one steroidogenic gene expression product or enzyme activity is selected from CYP21A2, CYP11A1, CYP17A1, CYP19A1, 3-βHSD1, 3-βHSD2, 17-βHSD1, StAR, HMGR, CYP11B2, CYP11B1, 5α-Reductase 2, and SULT1E1 gene expression product or enzyme activity.

In another embodiment, the modulation in the level of the at least one steroid or steroidogenic gene expression product or enzyme activity is at least 10%, at least 15%, at least 20%, at least 25%, at least 30%, at least 35%, at least 40%, at least 45%, at least 50% at least 55%, at least 60%, at least 65%, at least 70%, at least 80%, at least 85%, or at least 90% more or less than control. In an embodiment, the modulation is an increase compared to control. In another embodiment, the modulation is a decrease compared to control.

The control is, for example, the same assay performed in the absence of test substance (e.g. no test substance is added to the cell been added), or solvent or carrier (e.g. the solvent or carrier the test substance is dissolved in is added to the steroidogenesis cell).

A person skilled in the art will be familiar with assays that can be employed to determine the level of a steroid or steroidogenic gene product (e.g. mRNA, protein concentration) or enzyme activity. In an embodiment, an antibody-based method is used to directly or competitively detect the level of steroid. In an embodiment the antibody or other agent to detect the steroid level is labeled.

A label bound to the antibody or other agent to detect the steroid level is suitably capable of producing, either directly or indirectly, a detectable signal. For example, the label may be radio-opaque or a radioisotope, such as $^3$H, $^{14}$C, $^{32}$P, $^{35}$S, $^{123}$I, $^{125}$I or $^{131}$I; a fluorescent (fluorophore) or chemiluminescent (chromophore) compound, such as fluorescein isothiocyanate, rhodamine or luciferin; an enzyme, such as alkaline phosphatase, beta-galactosidase or horseradish peroxidase; acetylcholine esterase, an imaging agent; or a metal ion.

In another embodiment, the detectable signal is detectable indirectly. For example, a labeled secondary antibody can be used to detect the steroid of interest.

In an embodiment, the level of at least one steroid is detected by ELISA, optionally automated ELISA, immunoblotting or liquid chromatography mass spectrometry (LC-MS). Steroidogenic gene mRNA levels can be for example, determined by quantitative RT-PCR methods, and/or northern blotting. In addition, arrays (including microarrays for example, for detecting mRNA) can be used. Spectrometry methods can also be used. Protein expression levels of steroidogeneic genes can be determined for example by ELISA or immunoblotting. Furthermore, enzyme activity of steroidogenic enzymes can be determined using substrate conversion assay such as the tritium release assay or cellular incorporation and metabolism of E2, for example as described in the Examples below.

In an embodiment, the screening assay is a steroidogenesis modified H295R steroidogenesis assay, wherein the steroidogenesis modified H295R cell is used in a steroidogenesis assay described herein or known in the art.

In an embodiment, the object of the Steroidogenesis modified H295R Steroidogenesis Assay is to detect substances that affect for example androgen or estrogen steroid hormone productions of steroidogenesis modified H295R cells. The assay can detect substances that inhibit the enzymes of the steroidogenesis pathway and substances that induce enzymes responsible for hormone synthesis by measuring concentrations of e.g. estradiol, estrone, androstenedione, testosterone and dihydrotestosterone in medium after at least 1, 3, 6, 12, 24, 48, 60, and at least 72 h addition of the test substance.

In an embodiment, the assay is performed under standard cell culture conditions in 24 or 48 culture well plates. In another embodiment, the assay can also be performed under standard cell culture conditions in 6, 12, 96 or 384 culture well plates. In another embodiment, cells are acclimatized for about 24 hours and exposed for about 48 hour to, for example 1 to 10 different concentrations. In an embodiment six or seven concentrations of the test substance are tested in triplicate. In another embodiment, a solvent and a known inhibitor and inducer of hormone production are run at one, two or three fixed concentrations as negative and positive controls. In an embodiment, the inhibitor of hormone production is prochloraz. In an embodiment, the inducer of hormone production is forskolin. At the end of the exposure period, the medium is in an embodiment removed from each well and cell viability in each well is analyzed after removal of medium. In an embodiment photomicrographs of cells in the wells are taken prior to removal of medium for the purpose of cell viability assessment to enable retrospective analysis of cell conditions. Concentrations of hormones in the medium can be measured using a variety of methods including for example antibody based immunoassays such as enzyme linked immuno assays (ELISA) and radio immuno assays (RIA) and other bioanalytical hormone detection assays known to persons skilled in the art, and/or instrumental techniques such as liquid chromatography-mass spectrometry (LC-MS) or gas chromatography-mass spectrometry (GC-MS).

In an embodiment, data are expressed as fold change relative to the solvent control and the lowest observed effect concentration (LOEC), no observable effect concentration (NOEC), relative potencies compared to model compounds, and effective concentrations (EC) are reported. If the assay is negative, the highest concentration tested is reported as the no observable effect concentration (NOEC). Conclusions regarding the ability of a chemical to affect steroidogenesis in an embodiment, based on three independent test runs.

In an embodiment, steroidogenesis cells, for example the steroidogenesis modified H295R cells are plated in a 24 well plate. In another embodiment, steroidogenesis cells, for example the steroidogeneis modified H295R cells are incubated at 37° C. to allow cells to attach to the wells. In an embodiment, after about 8, about 16 or about 24 hours, the medium is replaced with fresh medium. Cells are then exposed to the test substance by adding for example 0.1% v/v (e.g. 1 microliter for 24 well plate) of a stock solution in DMSO/mL of medium (e.g in the well). In an embodiment, solvent controls receive 0.1% v/v (e.g. 1 microliter for 24 well plate) DMSO/mL of medium. The plate is optionally incubated for about 6, about 12, about 24, about 36, about 48, about 60 or about 72 hours at 37 C.

In another embodiment, the medium is removed and optionally aliquoted and optionally frozen at <−20° C., at <−80° C. and at <−196° C.

In another embodiment, a standard curve is run.

Final hormone concentrations are calculated for example as described in Example 7.

In an embodiment, to evaluate the relative increase/decrease in hormone production, the results are normalized to the mean solvent (SC) value of each test plate and results expressed as changes relative to the SC in each test plate.

If the data are normally distributed or approximate a normal distribution, differences between test substance treatments and solvent controls are analysed using a parametric test (such as Dunnett's Test). If the data are not normally distributed, an appropriate non-parametric test is used (e.g. Kruskal Wallis, Steel's many-one rank test). Relative changes are for example calculated as follows: Relative change=(concentration in well/average concentration of SCs in same plate)

In an embodiment, a test substance is positive if the fold induction is statistically different from the solvent control at doses that fall within the increasing or decreasing portion of the concentration response curve. For example, statistically significant increases in fold induction indicates the test substance is an inducer of one or more enzymes in the steroid synthesis pathway and statistically significant decreases in fold induction indicate the test substance is an inhibitor of one or more enzymes in the steroidogenesis pathway.

The steroidogenesis cell for example the steroidogenesis modified H295R cells can be used in a steroidogenesis assay that assesses steroidogenic enzyme activity, for example by assessing steroid metabolism and steroid cellular incorporation. In another aspect, the disclosure provides a method of screening for the effect of a test substance on the rate of metabolism of a steroid comprising:
   a) contacting a steroidogenesis cell, for example a steroidogenesis modified H295R or H295 cell of the present disclosure with the test substance in culture medium;
   b) removing the test substance, optionally by washing the cells;
   c) contacting the cell with a labeled steroid, optionally a radiolabeled steroid;
   d) separating water soluble steroid metabolites from the intact steroid by solvent extraction, optionally using dichloromethane (DCM);
   e) detecting a level of a water soluble labeled steroid metabolite; and
   f) determining the rate of steroid metabolism, wherein the rate of steroid metabolism is determined by the rate of formation of water soluble steroid metabolites.

In another embodiment, the test substance and the radiolabeled steroid are added simultaneously. Accordingly, the disclosure provides in an embodiment, a method of screening for the effect of a test substance on the rate of metabolism of a steroid comprising:
contacting a steroidogenesis cell such as a steroidogenesis modified H295R or H295 cell of the present disclosure with a labeled steroid, optionally a radiolabeled steroid together with the test substance;
separating water soluble steroid metabolites from the intact steroid by solvent extraction, optionally using dichloromethane (DCM);
detecting a level of a water soluble labeled steroid metabolite; and
determining the rate of steroid metabolism, wherein the rate of steroid metabolism is determined by the rate of formation of water soluble steroid metabolites.

In another aspect, the disclosure provides a method of screening for the effect of a test substance on cellular incorporation of a steroid comprising:
   a) contacting a steroidogenesis cell, for example a steroidogenesis modified H295R or H295 cell of the present disclosure with the test substance in culture medium;
   b) removing the test substance, optionally by washing the cells;
   c) contacting the cell with a labeled steroid, optionally a radiolabeled steroid;
   d) removing extracellular labeled steroid, optionally by washing the cells;
   e) homogenizing the cells; and
   f) detecting intracellular labeled steroid;
   wherein the cellular incorporation of labeled steroid is evaluated by the radioactivity of the cell homogenates.

In an embodiment, the test substance and labeled steroid are added simultaneously. Accordingly, in an embodiment, the disclosure provides a method of screening for the effect of a test substance on cellular incorporation of a steroid comprising:
   a) contacting a steroidogenesis cell, optionally a steroidogenesis modified H295R or H295 cell of the present disclosure with a labeled steroid, optionally a radiolabeled steroid together with the test substance;
   b) removing extracellular labeled steroid, optionally by washing the cells;
   c) homogenizing the cells; and
   d) detecting intracellular labeled steroid;
   wherein the cellular incorporation of labeled steroid is evaluated by the radioactivity of the cell homogenates.

In an embodiment, test substance induced effects on cellular incorporation and metabolism of E2 are evaluated. In another embodiment, the effects are evaluated using radiolabeled estradiol (Modified from Lancon et al. 2004). For example, after at least 1, at least 3, at least 6, at least 12, at least 24, at least 48, at least 60 or at least 72 h exposure, the steroidogenesis cells (e.g. the steroidogenesis modified H295R cells) are washed twice and then are incubated with supplemented medium comprising labeled steroid, for example comprising 1 nM 6,7 [$^3$H]-E2 (Perkin Elmer, Boston, Mass.) and a test substance if for direct exposure. In an embodiment, DMSO is used as the carrier solvent and does not exceed 0.1% v/v. In another embodiment, after incubation, for example incubation for 30 min at 37° C. and 5% $CO_2$, cells are placed on ice to stop the reaction. Cell culture media are collected for extraction by adding for example 200 µL of medium into 500 µL dichloromethane (DCM). Supernatant (medium) is collected for hormone measurement for example by scintillation as described elsewhere. In an embodiment, E2 metabolism activity is determined. For example, the E2 metabolism activity is determined by the rate of formation of water soluble E2 metabolites. In an embodiment, after removal of medium the cells remaining in the plate are washed two times with ice-cold PBS buffer. In an embodiment, lysis buffer for example 250 µL of lysis buffer containing 0.1 M NaOH, 0.1% SDS and 0.1% $Na_2CO_3$ is added to each well to lyse the cells for example for about 15 min at room temperature. In another embodiment, the cellular incorporation of estradiol is evaluated by the radioactivity of the cell homogenates.

IV. Kits and Systems i) Detection Kits for Endocrine Disruptors

In another aspect, the disclosure provides a kit for screening for an endocrine disruptor comprising a cell disclosed herein and an analyte specific detection agent for determining the level of at least one steroid.

The analyte specific detection agent for determining the level of at least one steroid, for example, comprises an antibody that binds the steroid, or an ELISA for the steroid.

In an embodiment, the kit comprises an analyte specific detection agent for determining the level of at least one steroid or a kit control e.g. a standard such as a quantity of a steroid such as estradiol for example that can be used for calibration and/or comparison.

In another embodiment, the kit comprises one or more of phosphate-buffered saline (PBS), trypsin, dimethylsulfoxide (DMSO), and/or model compounds such as forskolin and/or prochloraz which can be used as controls. In another embodiment, the kit comprises a known quantity of one or more steroids for use as a standard, for example when detecting steroid levels by liquid chromatography (LC) and/or mass spectrometry (MS).

Other items that can be included in a kit include for example reagents to assess cell viability, gene expression and/or enzyme concentrations and activities.

Gene expression can be for example, determined by quantitative real time-polymerase chain reaction (RT-PCR) methods (e.g. using SYBR Green, EvaGreen, Molecular becon or Taqman probes), and/or northern blotting.

Cell viability assays use different biomarker detection to quantify the number of both live and dead cells, such as the MTT assay. The MTT assay are laboratory tests and standard colorimetric assays (an assay which measures changes in color) for measuring the activity of enzymes that reduce MTT (3-(4,5-Dimethylthiazol-2-yl)-2,5-diphenyltetrazolium bromide, a tetrazole) to formazan, giving a purple color.

Another aspect provides a composition comprising a steroidogenesis modified cell for example a steroidogenesis modified H295R cell of the present disclosure and a suitable buffer or carrier. In an embodiment, the modified cell is lyophilized. In another embodiment, the modified cell is frozen and optionally resuspended in a suitable buffer. In another embodiment, the modified cell is in culture. In an embodiment, a suitable buffer comprises cell culture medium.

ii) System for Predicting Mechanism of Action of EDC

In an embodiment of the present disclosure, the profiles of steroid production in the modified cell lines of the present disclosure in the presence of known substances will be used as "fingerprints". A database will be built to house such fingerprints. After the chemical-caused profile of steroid productions are collected, strategies will be applied to search in the database for a profile that is a "best match" for a test compound, which could indicate the mechanisms of action of that test compound.

Accordingly, another aspect of the disclosure provides a system for predicting the mechanism of action of an endocrine disruptor with unknown mechanism comprising:
  (i) a control module for receiving a steroid production profile for the endocrine disruptor wherein the steroid production profile is obtained by contacting the endocrine disruptor with a steroidogenesis cell, optionally a steroidogenesis modified cell, preferably a steroidogenesis modified H295R cell and determining a level of at least one steroid or steroidogenic gene mRNA, protein or enzyme activity produced by the cell line;
  (ii) a database comprising steroid production profiles for a plurality of reference endocrine disruptors;
  (iii) an analysis module for comparing the steroid production profile of the endocrine disruptor with the steroid production profiles of the plurality of reference endocrine disruptors; and
for identifying a best match for the steroid production profile of the endocrine disruptor with the steroid production profiles of the plurality of reference endocrine disruptors,
wherein the mechanism of action of the best match reference endocrine disruptor is predicted to be the mechanism of action of the endocrine disruptor.

The following non-limiting examples are illustrative of the present disclosure:

EXAMPLES

Example 1

A method to increase the accuracy and precision of the measurement of basal production of E2 as well as allow for greater sensitivity to detect the inhibitory effects of chemicals and to better discriminate among chemicals is needed. To achieve this goal two approaches were considered and applied. The first was to reduce the LOQ for ELISA and LC\MS-MS. While improvements in both methods have been achieved, the improvement was not deemed to be sufficient and the procedures were more time consuming. The alternative approach considered was to enhance the production of E2 released into the medium.

Progesterone and 17α-hydroxyprogesterone are the common precursors of mineralocorticoids, glucocorticoids, T and E2 (FIG. 1). Steroid 21-hydroxylase (CYP21) is an essential enzyme for the biosynthesis of mineralo- and glucocorticoids by converting progesterone and 17α-hydroxyprogesterone to 11-deoxycorticosterone (mineralocorticoid pathway) and 11-deoxycortisol (glucocorticoid pathway), respectively (Sasano et al., 1988). These precursors, in turn, are converted to the biologically active hormones aldosterone and cortisol by aldosterone synthetase (CYP11B2) and steroid 11b-hydroxylase (CYP11B1), respectively. It was hypothesized that genetic inhibition of the CYP21 gene will reduce the biosynthesis of mineralo- and glucocorticoids and accumulate more substrates for Zona reticularis pathways, which should lead to greater production of the steroid hormones of interest, testosterone, androstenedione, dihydrotestosterone, estrone and E2 by H295R cells. Such an inhibition would improve the accuracy and precision of measurements of these hormones and make H295R cells more sensitive to determine the inhibitory effects of chemicals on steroid hormone production and metabolism. To test this hypothesis, the following experiments were conducted: 1) genetically inhibit the CYP21A2 gene in H295R cells by use of siRNA and develop a stable H295R in which expression of CYP21A2 was knocked down; 2) to characterize the new H295R/CYP21A2 knockdown (H295R/CYP21A2-KD) cells, 3) compare production of steroid hormones, especially E2, to that of the parent H295R cells by measuring both the amount of CYP21A2 protein, and steroid hormone concentrations in the medium. The results are described in several of the following examples.

Methods of Producing Cell Lines

Construct

The shRNA constructs were designed to include a hairpin of 21 base pair sense and antisense stem and a 6 base pair loop. Each hairpin sequence was cloned into a lentiviral vector and sequence verified. Multiple constructs were created per gene to ensure adequate coverage of the target gene. Rules-based shRNA design allows for efficient gene knockdown. The lentiviral vector allows for consistent high expression of the shRNA constructs in the cells and contains antibiotic resistance marker to allow stable selection. The human CYP21A2 pLKO.1 lentiviral shRNA vector was ordered from Thermo Scientific Open Biosystems (Huntsville, Ala. USA). The sequences of the shRNA molecules are available online (http://www.openbiosystems.com). The siRNA (small interfering RNA) or shRNA (short hairpin) is a recently well-developed technology, and many other companies also provide similar products such as:

Santa Cruz Biotechnology, Inc (www.scbt.com)
Ambion (www.ambion.com)
Invitrogen (www.invitrogen.com)
Signosis BioSignal Capture (www.signosisinc.com)

Cell Culture and Transfection

The culture and maintenance of H295R cells (ATCC, Beltsville, Md.) was following the protocol previously described (Hecker et al. 2006; Hilscherova et al. 2004; Zhang et al. 2005). Briefly, H295R cells were cultured in Dulbecco's modified Eagle's medium supplemented with Ham's nutrient mixture F-12 (Sigma, St. Louis, Mo.) with 1 ml/100 ml ITS+ Premix (BD Bioscience, San Jose, Calif.) and 2.5% BD Nu-Serum (BD Bioscience, San Jose, Calif.) at 37° C. in a 5% $CO_2$ atmosphere. For transfection, cells were seeded onto 6-well plates and were transfected with human CYP21A2 pLKO.1 lentiviral short hairpin RNA (shRNA) (Thermo Scientific Open Biosystems, Huntsville, Ala. USA) by Arrest-In transfection reagent (Thermo Scientific Open Biosystems, Huntsville, Ala. USA) for 5 h. After two d of culture, transfected cells were selected using culture medium containing 0.4 ug/mL puromycin (Sigma, St. Louis, Mo.) for an extended selection period (>3 weeks). Surviving cells were expanded and tested for production of various steroids.

1. Hormone Measurement

For instrumental detection of steroids, culture medium samples were extracted by ethyl acetate/hexane (v/v, 50/50) followed by LC-MS/MS analysis. Surrogate deuterated standards, Estrone-d4, Estradiol-d4, Testosterone-d5, Androstenedione-d7, Progesterone-d9, 17αOH Progesterone-d8, 21αOH Progesterone-d8 and Cortisol-d4 were spiked into samples before the extraction. C-d4 was provided by Cambridge (Andover, Mass., USA), other labelled standards were provided by C/D/N Isotope (Pointe-Claire, Quebec, Canada). Test chemicals (e.g. test substances) were obtained from Sigma. For E1 and E2, the mobile phase was consisting of acetonitrile and 0.1% formic acid in water. For all other hormones, chromatography was performed using a nanopure water and methanol. Sample extract was separated by a 100 mm×2.1 mm Thermo Scientific Betasil C18 column (5 μm pore size) and then analyzed by a triple quadruple tandem mass spectrometer (Waters, USA). All data were acquired and processed with Analyst Software, Ver. 1.4.1 (ABI-Sciex).

ELISA measurement of testosterone and estrogens was conducted as previously described (Hecker et al. 2006). Briefly, the hormones were extracted twice with diethyl ether (5 ml) and solvent was evaporated under a stream of nitrogen. The residue was dissolved in ELISA assay buffer and was measured by competitive ELISA using the manufacturer's recommendations (Cayman Chemical Company, Ann Arbor, Mich.; Testosterone [Cat #582701], 17β-Estradiol [Cat #582251]).

2. Statistical Analysis

Prior to conducting statistical comparisons, data were tested for normality using the Shapiro-Wilkes test and probability plots. If necessary, values were log-transformed to approximate normality. Two-sample comparisons were made by use of student t test. A linear regression model was used to compare the hormone production in the two cell lines in response to chemical exposure. Statistical analysis was conducted using the R project language (http://www.r-project.org/). Differences with $p<0.05$ were considered to be statistically significant.

Western Blotting

After determination of the total protein concentration, aliquots of cell lysate were electrophoresed on 8% SDS-PAGE gel, and then electro-blotted onto a 0.45 μm pore size nitrocellulose membrane as previously described (Zhang et al. 2009). The nitrocellulose membrane was blocked in skimmed milk, and then was incubated with the goat anti-human CYP21A2 (C-17) antibody (Santa Cruz Biotechnology, Inc. USA). Immunoblots were detected by anti-rabbit IgG conjugated with horseradish peroxidise (HRP)— using an ECL Plus kit (Amersham) and visualized using the VersaDoc Imaging System 4000 (BioRad, CA, USA).

Results

Establishment of a Stable H295R/CYP21A2-KD Cell Line.

Figure 2:
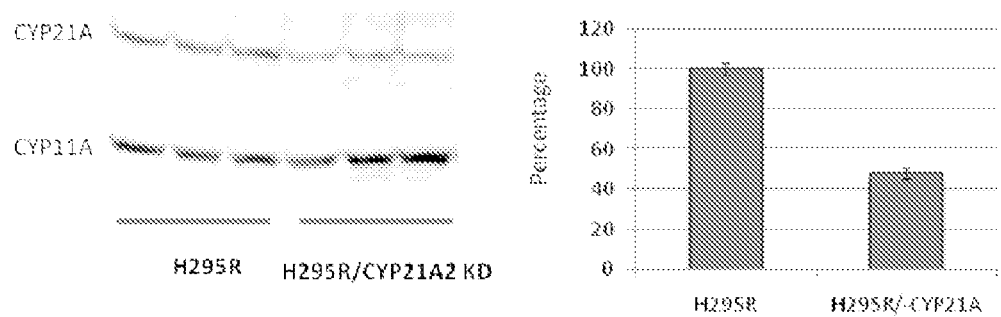
FIG. 2 Western blot analysis of human CYP21A2 protein expression in the stable H295R/CYP21A2-KD and unaltered H295R cells. Unrelated CYP11A protein detected on the same plot membrane was used as a reference. Values presented are means+/−standard deviation.

A steroidogenesis modified H295R cell line, H295R/CYP21A2-KD, was developed by using a human CYP21A2 pLKO.1 lentiviral shRNA plasmid construct carrying a selection marker. Stable transfected colonies were selected with puromycin and followed by further expansion. The puromycin-resistance of the stable H295R/CYP21A2-KD was preserved after multiple freezing-thaw cycles, which confirmed the stable transfection with the plasmid carrying the siRNA. The knockdown of CYP21A2 was confirmed by western blotting (FIG. 2). CYP21A2 protein level was 48% in the stable knockdown cell line relative to the parental H295R cells. Instrumental measurement of concentration of different steroids in the culture medium displayed that both cell line produce similar level of progesterone within 48-h incubation. The stable H295R/CYP21A2-KD cell line produced ~10 fold more T and greater than 15-fold more E1 and E2, relative to that of the unaltered H295R cells (Table 4).

Although the H295R cell has been identified as one of the best in vitro assays to assess chemical induced effects on steroidogenesis, and was very effective in detecting chemicals that increased production of E2, it had been limited in its ability to detect decreases in production of E2. This was due to the fact that the most potent estrogen E2 is detected at relatively small concentrations (~10-50 pg/ml in cell culture medium) by H295R cells under standard culture condition.

Since the LOQs for E2 by current ELISA and LC\MS-MS is approximately 2-10 pg E2/ml, it was difficult to accurately measure decreases in production of E2. Also, the observed great variance around the LOQ further reduced the sensitivity of the H295R assay to detect inhibition of E2 production by chemicals. Therefore, an increase at the basal production of E2 was deemed to be useful in improving sensitivity as well as accuracy and precision of the H295R assay.

CYP21A is a protein localizes to the endoplasmic reticulum and hydroxylates steroids at the 21 position. Its activity is required for the synthesis of steroid hormones including cortisol and aldosterone. There are two CYP21A genes in human genome, CYP21A1P and CYP21A2, respectively. Human CYP21A1 is a pseudo gene and has lost its protein-coding ability. Human CYP21A2 encode the cytochrome P450 family 21 enzyme and mutations in this gene cause congenital adrenal hyperplasia, which is an autosomal recessive disorder caused by defective adrenal steroid biosynthesis, resulting in reduced glucocorticoid and increased androgen production (Merino et al., 2007). The stable H295R/CYP21A2-KD cells are significant improvement in the utility of the H295R cells for detecting decreases in E2 production without altering the structure of the endogenous steroidogenesis pathway or affecting the pattern of responses to model EDCs. Thus, the stable H295R/CYP21A2-KD cells that overcome the limitations in basal E2 production by H295R cells improved sensitivity such that it is now possible to detect weak inhibitors of E2 production. The newly developed H295R/CYP21A2-KD cells are a superior screening tool that outperforms the original H295R cells and makes the knockdown cells preferable for application as part of the EDSP and other national and/or international screening programs.

FIG. 2 Western blot analysis of human CYP21A2 protein expression in the stable H295R/CYP21A2-KD and unaltered H295R cells. Unrelated CYP11A protein detected on the same plot membrane was used as a reference. Values presented are means+/−standard deviation.

Example 2

Gene Knock Downs of Other Enzymes Important for Steroidogenesis

The knock down cell lines listed in Table 1 were developed using the methods described in Example 1 to examine the gene knock-down on the production of different hormones, which can serve to assess EDCs and serve as models to simulate the enzyme inhibition by endocrine disrupting chemicals. The shRNA nucleic acids used to make these cell lines are listed in Table 2. The expected cell properties are listed in Table 5. Cell properties were confirmed for the CYP19A1 KD and the CYP17A1 KD. The CYP19A KD was confirmed with less production of Estrone (E1) which is a metabolite of estradiol suggesting E1 and E2 levels are reduced as predicted the CYP17A KD was confirmed with increased production of 21a hydroxyprogesterone and less production of 17 hydroxyprogesterone, androstenedione, testosterone and estrone, confirming increased production progesterone and decreased production of sex steroids as predicted.

These cell lines will be incorporated into mathematical and statistical models to evaluate the endocrine disrupting potency of environmental chemicals (Zhang, X., Newsted, J. L., Hecker, M., Higley, E. B., Jones, P. D., and Giesy, J. P. (2009). Classification of chemicals based on concentration-dependent toxicological data using ToxClust. *Environ. Sci. Technol.* 43(10), 3926-3932.).

Example 3

Multiple Gene Knockdowns

Similar methods to those described in Example 1 will be used to make steroidogenesis modified H295R cells with multiple gene knockdowns. The genes to be knocked down include for example, any two or more genes listed in Table 1. For transfection, cells are seeded onto 6-well plates and are transfected with single vector carrying multiple shRNA constructs for 5 h. After two d of culture, transfected cells are selected using culture medium containing 0.4 ug/mL puromycin (Sigma, St. Louis, Mo.) for an extended selection period (>3 weeks). Surviving cells are expanded and tested for production of various steroids.

As an example, H295R/CYP21A2&SULT1E1 knockdown cell aims to knockdown the protein expression of CYP21A2 and SULT1E1. SULT1E1 is a sulfotransferase enzyme which catalyzes the sulfate conjugation of estrogen. Simultaneous knockdown of both CYP21A2 and SULT1E1 can further raise the basal sexual steroid production and thereby increases the sensitivity of the steroidogenesis assay in the detection of endocrine disruptors.

Example 4

Steroidogenesis Assay Using Steroidogenesis Modified H295R Cells

Because it simultaneously expresses all of the genes involved in synthesis and conversion of steroid hormones, the H295R human adrenocortical carcinoma cell line has been suggested as a useful in vitro assay for examining effects of chemicals on the adrenal and the general process of steroidogenesis. The H295R steroidogenesis assay has been approved for use in the tiered screening approach developed by the USEPA. It has been approved to test chemicals for endocrine disrupting effects of chemicals in the current Tier I tests of EPA's Endocrine Disruptor Screening Program (EDSP) and is currently in its last phase of validation through OECD as an international standard assay. The endpoints of the current assay are production of two sexual hormones, testosterone and 17β-estradiol, but effects on mRNA expression of steroidogenic genes has also been used as an endpoint. However, concentrations of 17β-estradiol, (E2) is produced at relatively small (~10-50 pg/ml in cell culture medium) and difficult to measure by automated ELISA methods. Therefore, a knockdown version of the H295R cells in which endogenous production of testosterone, estrone and E2 were enhanced by genetically reducing the expression of CYP21A2 which can use the same precursors of sexual hormone, pregnenolone and progesterone to synthesize mineralo- and glucocorticoids. The resulted stable H295R CYP21A2 knockdown (H295R/CYP21A2-KD) cell line produces more than 10-fold greater concentrations of the steroid hormones testosterone, estrone and 17β estradiol in the culture medium but the same level of progesterone as the parent H295R cells. Furthermore, stable H295R/CYP21A2-KD cells displayed the same response to the inducer (forskolin) and inhibitor (prochloraz) as did unaltered H295R cells. In addition, other stable steroidogenesis modified H295R cell lines comprising reduced expression of other steroidogenesis pathway enzymes have also been constructed. Therefore, stable steroidogenesis modified H295R cells will provide a unique and significantly improved screening assay by increasing both the accuracy and precision compared to unaltered H295R cells.

Model Chemicals, e.g. Forskolin and Prochloraz.

Chemical Exposure

Cells were exposed to model chemicals in 24-well cell culture plates (COSTAR, Bucks, UK). One ml of cell suspension was added to each well and cells cultured for 24 to 48 h. Cells were exposed to chemicals dissolved in dimethyl sulfoxide (DMSO; Sigma-Aldrich, St. Louis, Mo.). Forskolin (FOR) was obtained from Sigma Chemical Co. (St. Louis, Mo., USA) and Prochloraz (PRO) was purchased from Aldrich (St. Louis, Mo., USA). The culture medium was collected from each well after 48 h and stored at −80° C. until further measurement.

Results

Chemical Exposure

Figure 3:
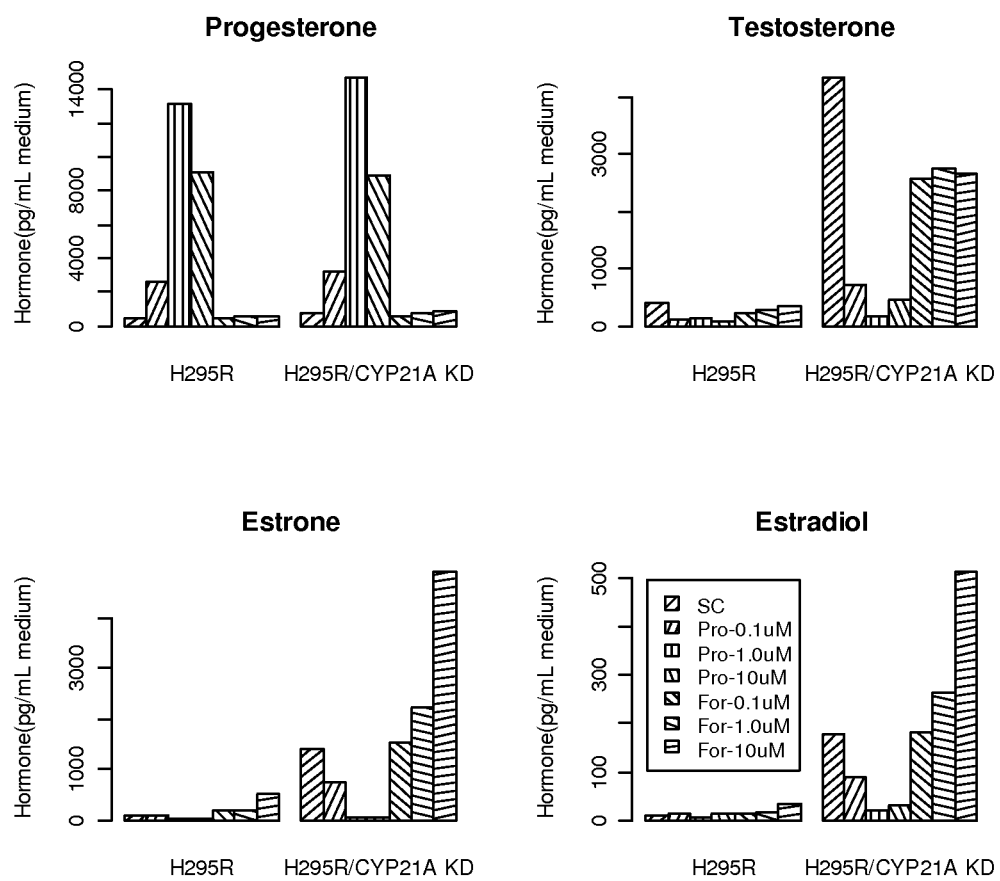
FIG. 3 Production of progesterone (P), T, E1 and E2 in H295R and H295R/CYP21A2-KD cell line after exposure to forskolin (FOR) and prochloraz (PRO). SC: Solvent Control.
Figure 4:
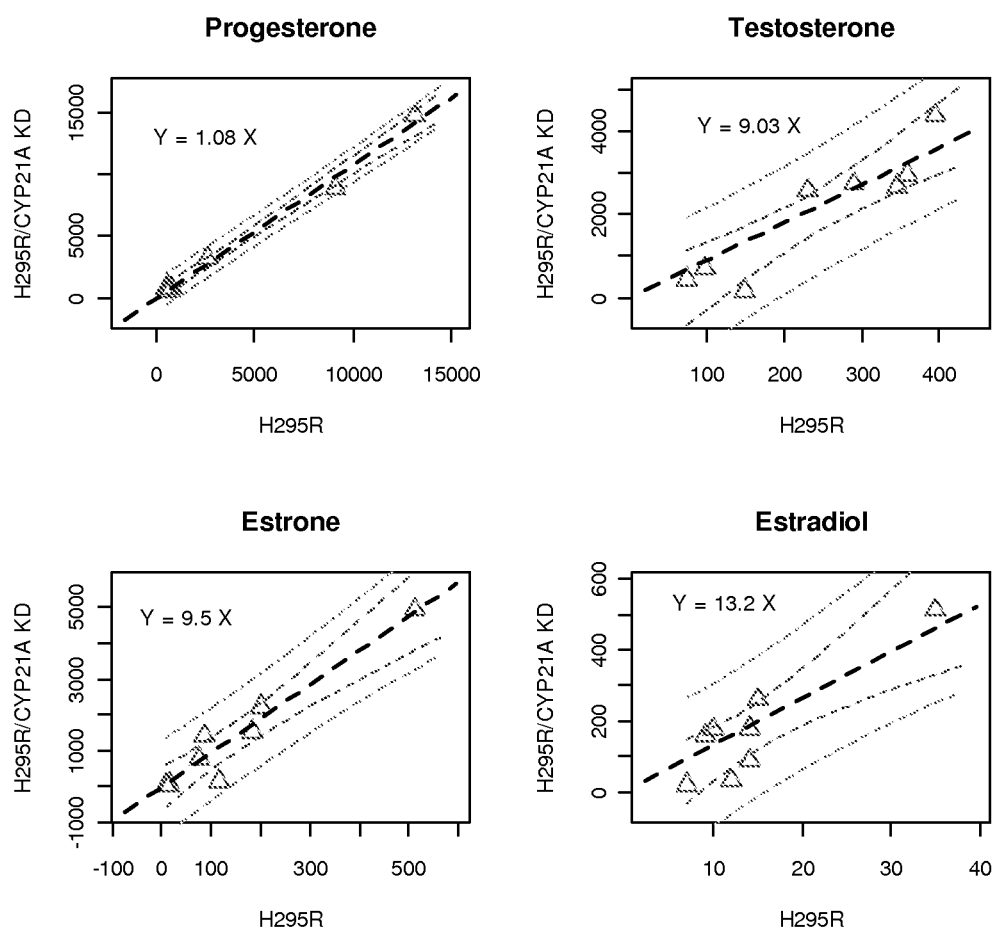
FIG. 4 Comparison of the hormone production (pg/mL) between the H295R/CYP21A2-KD and unaltered H295R cells under the same chemical exposure conditions.

Unaltered H295R and stable H295R/CYP21A2-KD cells were exposed to several concentrations of forskolin and prochloraz for 48 h and concentrations of different steroids were measured in the culture medium. H295R/CYP21A2-KD cells exhibited similar fold modulation responses to the chemical exposure as unaltered H295R cells (FIG. 3). Exposure to 0.1 µM to 10 µM prochloraz increased concentrations of progesterone production in both H295R and H295R/CYP21A2-KD cells in a dose-dependent manner. Production of T, E1 and E2 was inhibited by prochloraz in the both cell types. Comparable increases in concentrations of T, E1 and E2 by forskolin was also observed in the two cell types. Further analysis using linear regression model suggested that concentration of all four measured steroids in stable H295R/CYP21A2-KD cell line were significantly correlated to that in the unaltered H295R cells (FIG. 4).

Discussion

In response to emerging concerns that substances may alter the function of endocrine systems and result in adverse effects to human health, many countries and international organizations have developed strategies to test and evaluate the potential endocrine disrupting chemicals (ECDs). The USEPA has been developing and validating in vitro and in vivo assays to determine the potential of chemicals to interact with the endocrine systems and related functions in humans and wildlife. The EPA is recommending a two-tiered approach in the evaluation process. The Tier I Screening battery of assays is based on EPA's Endocrine Disruptor Screening and Testing Advisory Committee (EDSTAC) recommendations and aims to identify chemicals affecting the estrogen, androgen & thyroid hormone systems. Tier 2 testing is intended to confirm, characterize and quantify those effects for estrogen, androgen and thyroid active chemicals. Included in the Tier 1 Screening battery is the H295R Steroidogenesis Assay which uses the H295R human adrenocortical carcinoma cell line. Furthermore, the H295R Steroidogenesis Assay is currently in the last validation phase of the Test Method Validation Program for the Organization for Economic Cooperation & Development (OECD), which will ultimately result in the development of an OECD Test Guideline for assessing the potential of chemicals to affect steroid hormone synthesis.

Example 5

Figure 5:
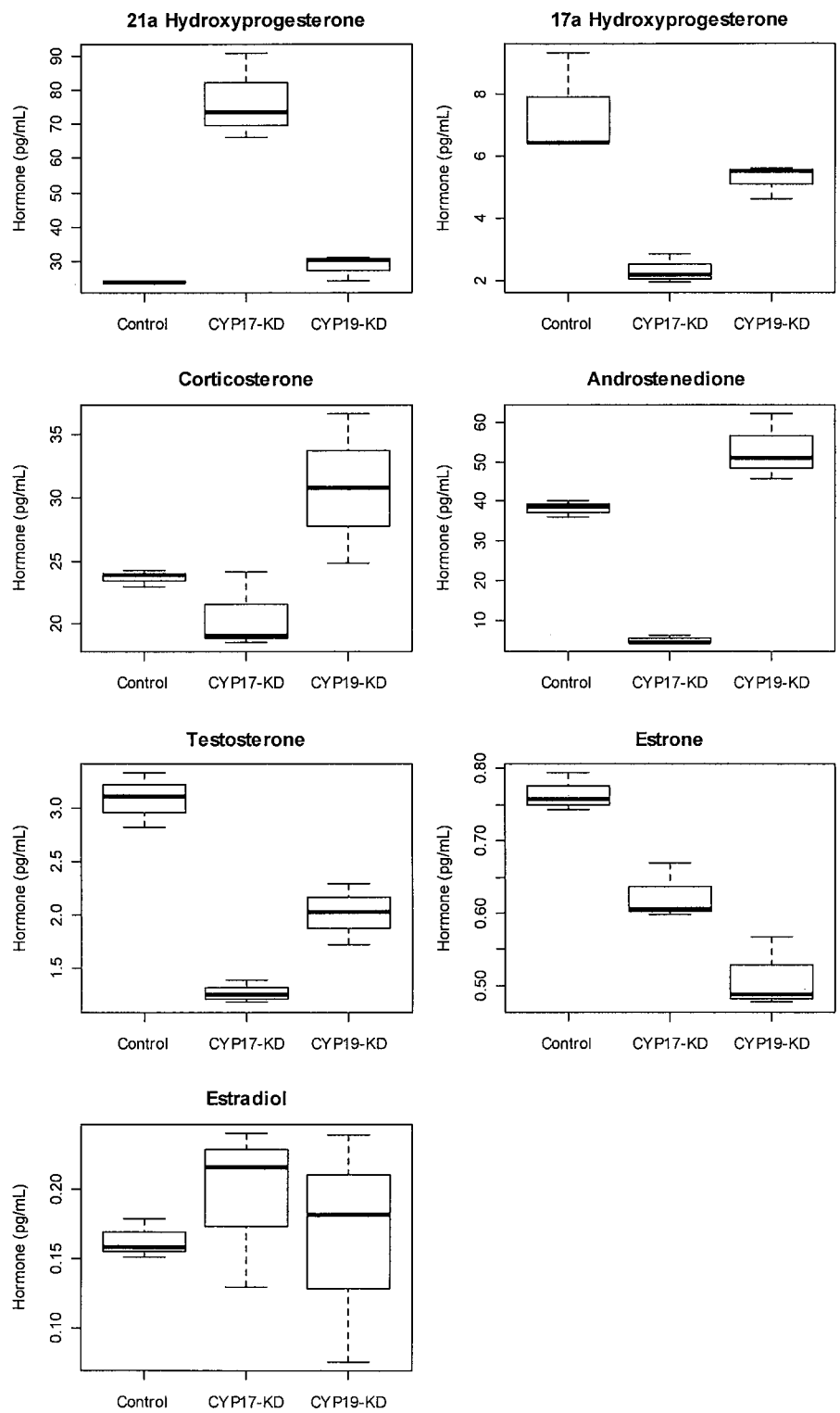
FIG. 5 Comparison of the hormone basal production (pg/mL) between H295R/CYP17-KD, H295R/CYP19-KD and unaltered H295R cells.

Two other knockdown cell lines, CYP17A-KD and CYP19A-KD, were tested for their level of steroids production (see FIG. 5). CYP17A is the enzyme converting progesterone into 17a hydroxyprogesterone, and it also catalyzes the conversion from 17a hydroxyprogesterone to androstenedione. As indicated in FIG. 5, CYP17A knockdown in H295R resulted in favorable results, in which both 17a Hydroxyprogesterone and androstenedione production were significantly reduced comparing to control. On the other hand, the production of 21a hydroxyprogesterone was significantly enhanced. In the CYP19A-KD h295R cells, the level of estrone was significantly lower comparing to the control cell line.

In both these KD cells lines, favorable properties have been achieved. The steroid production profiles have great value to test chemicals and to predict chemicals induced effect on the steroidogenesis pathway.

Example 6

The basal production of steroids in other two different steroidogenic cell lines, JEG-3 and R2C have recently been determined. JEG-3] and R2C cells secrete increased levels of Estradiol (E2) compared to H295R cells (see Table 6). R2C cells also secrete increased levels of 17a hydroxyprogesterone. These cell lines, can also be further modified according to the methods described herein to knock down expression of one or more steroidogenesis genes. Modified or unmodified R2C and/or JEG-3 cells can be used for example in place of modified H295R cells in the methods described herein.

Example 7

Method for Detecting Steroid Cellular Intake and Metabolism Using H295, H295R or Steroidogenesis Modified H295R Cells Chemical induced effects on cellular incorporation and metabolism of E2 are evaluated using radiolabeled estradiol (Modified from Lancon et al. 2004). After 48 h exposure steroidogenesis modified H295R cells are washed twice and then are incubated with 0.25 ml of supplemented medium containing 1 nM 6,7 [$^3$H]-E2 (Perkin Elmer, Boston, Mass.) and chemicals if for direct exposure. DMSO is used as the carrier solvent and does not exceed 0.1% v/v. After 30 min incubation at 37° C. and 5% $CO_2$, cells are placed on ice to stop the reaction. Cell culture media are collected for extraction by adding 200 µL of medium into 500 µL DCM. After vortexing, 100 µL of supernatant (medium) is collected for the scintillation measurement as described above. The E2 metabolism activity is determined by the rate of formation of water soluble E2 metabolites. Immediately after removal of medium the cells remaining the plate are washed two times with ice-cold PBS buffer. 250 µL of lysis buffer containing 0.1 M NaOH, 0.1% SDS and 0.1% $Na_2CO_3$ is added to each well to lyse the cells for 15 min at room temperature. The cellular incorporation of estradiol is evaluated by the radioactivity of the cell homogenates.

Example 8

Steroidogenesis Modified H295R Steroidogenesis Assay

The object of the Steroidogenesis modified H295R Steroidogenesis Assay is to detect substances that affect for example androgen or estrogen steroid hormone productions. The assay can detect substances that inhibit the enzymes of the steroidogenesis pathway and substances that induce enzymes responsible for hormone synthesis.

The assay is performed under standard cell culture conditions in 24 culture well plates. Cells are acclimatized for 24 hours and exposed for 48 hour to six concentration of the test substance in triplicate. A solvent and a known inhibitor and inducer of hormone production are run at a fixed concentration as negative and positive controls. At the end of the exposure period, the medium is removed from each well. Cell viability or cytotoxicity in each well is analyzed after removal of medium. Concentrations of hormones in the medium can be measured using a variety of methods including bioanalytical immunoassays such as ELISA or RIA and/or instrumental techniques such as liquid chromatography-mass spectrometry (LC-MS). Data are expressed as fold change relative to the solvent control and the lowest observed effect concentration (LOEC). If the assay is negative, the highest concentration tested is reported as the no observable effect concentration (NOEC). Conclusions regarding the ability of a chemical to affect steroidogenesis should be based on three independent test runs. the first test run may function as a range finding run with subsequent adjustment of concentrations for runs 2 and 3 if solubility or cytotoxicity problems are encountered or the activity of the chemical seems to be at the extreme end of the range of the concentrations tested.

Steroidogenesis modified H295R cells are plated in a 24 well plate, incubated at 37 C to allow cells to attach to the wells. After 24 hours, the medium is replaced with fresh medium. Cells are exposed to the test substance by adding 1 microliter of a stock solution in DMSO/mL of medium. Solvent controls receive 1 microliter DMSO/mL of medium. The plate is incubated for 48 hours at 37 C.

The medium is removed and optionally aliquoted and optionally frozen.

Cell viability is determined for each exposure plate.

Hormone is analyzed using one of a variety of hormone detection systems such as ELISA, RIA or LC-MS.

A standard curve is run.

Final hormone concentrations are calculated for example as follows:

Example:

Extracted: 450 microliters,

Reconstituted in: 250 mL assay buffer;

Dilution in Assay: 1:10 (to bring sample within the line range of the standard curve);

Hormone concentration in Assay: 150 pg (already adjusted for final concentration per ml);

Recovery: 89%

Final hormone concentration=(hormone concentration (per mL)/recovery)(dilution factor)

Final hormone concentration=(150 pg×(250 microliters/450 microliters)×10/0.89=936.33 pg/mL To evaluate the relative increase/decrease in hormone production, the results should be normalized to the mean solvent (SC) value of each test plate and results expressed as changes relative to the SC in each test plate.

The average response in each well should be divided by the relative cell viability measured in the same well to normalize for possible differences due to variations in the number of live cells. If the data are normally distributed or approximate a normal distribution, differences between test substance treatments and solvent controls should be analysed using a parametric test (such as Dunnett's Test). If the data are not normally distributed, an appropriate non-parametric test should be used (e.g. Kruskal Wallis, Steel's many-one rank test). Relative changes should be calculated as: Relative change= (concentration in well/average concentration of SCs in same plate).

A test substance is positive if the fold induction is statistically different from the solvent control at doses that fall within the increasing or decreasing portion of the concentration response curve. Statistically significant increases in fold induction indicates the test substance is an inducer of one or more enzymes in the steroid synthesis pathway and statistically significant decreases in fold induction indicate the test substance is an inhibitor of one or more enzymes in the steroidogenesis pathway.

While the present disclosure has been described with reference to what are presently considered to be the preferred examples, it is to be understood that the disclosure is not limited to the disclosed examples. To the contrary, the disclosure is intended to cover various modifications and equivalent arrangements included within the spirit and scope of the appended claims.

All publications, patents and patent applications are herein incorporated by reference in their entirety to the same extent as if each individual publication, patent or patent application was specifically and individually indicated to be incorporated by reference in its entirety.

TABLE 1

List of genes, which have been knocked down individually. Separate stable H295R knockdown cell lines have been developed for each individual gene.

| NO | Knockdown Gene | Entrez gene ID | Gene Function |
|---|---|---|---|
| 1 | CYP11A1 | 1583 | Cholesterol side-chain cleavage |
| 2 | CYP17A1 | 1586 | 17-hydroxylation, scission of the C-17,20 carbon bond |
| 3 | CYP19A1 | 1588 | Conversion of androgens to estrogens |
| 4 | CYP21A2 | 1589 | 21-hydroxylation |
| 5 | 3-βHSD1 | 3283 | 3β-hydroxysteroid dehydrogenation and isomerization |
| 6 | 3-βHSD2 | 3284 | 3β-hydroxysteroid dehydrogenation and isomerization |
| 7 | 17-βHSD1 | 3292 | NAD(H)- and/or NADP(H)-dependent enzymes that catalyze the oxidation and reduction of 17,-hydroxy- and 17,-ketosteroids respectively. |
| 8 | StAR | 6770 | Mediates cholesterol transport to the inner mitochondrial membrane (to CYP11A) |

TABLE 1-continued

List of genes, which have been knocked down individually. Separate stable H295R knockdown cell lines have been developed for each individual gene.

| NO | Knockdown Gene | Entrez gene ID | Gene Function |
|---|---|---|---|
| 9 | HMGR | 3156 | 4-electron reduction of HMG CoA into CoA and mevalonate-step leading to the cholesterol synthesis |
| 10 | CYP11B1 | 1584 | Making cortisol from 11-deoxycortisol |
| 11 | CYP11B2 | 1585 | 11- and 18-hydroxylation, 18-oxidation |
| 12 | 5α-Reductase 2 | 6716 | Catalyzing the conversion of testosterone to dihydrotestosterone |
| 13 | SULT1E1 | 6783 | Catalyzing the sulfate conjugation of many hormones, estrogen preferring |
| 14 | CYP3A4 | 1576 | CYP3A4 encodes a monooxygenase which catalyzes many reactions involved in drug metabolism and synthesis of cholesterol, steroids and other lipids. |
| 15 | UGT1A1 | 54658 | Encoding a UDP-glucuronosyltransferase that transforms small lipophilic molecules, such as steroids, and drugs, into water-soluble, excretable metabolites |

TABLE 2 shRNA sequences used in this study*

| Gene Name | Gene ID | shRNA Sequence | |
|---|---|---|---|
| CYP17A1 | 1586 | TGCTGTTGACAGTGAGCGCGGGCACAGAAGTT ATCATCAATAGTGAAGCCACAGATGTATTGATG ATAACTTCTGTGCCCTTGCCTACTGCCTCGGA | SEQ ID NO: 3 |
| 3-βHSD2 | 3284 | TGCTGTTGACAGTGAGCGACCACACAGTCACAT TATCAAATAGTGAAGCCACAGATGTATTTGATA ATGTGACTGTGTGGCTGCCTACTGCCTCGGA | SEQ ID NO: 6 |
| 17-βHSD1 | 3292 | TGCTGTTGACAGTGAGCGCGGGTGGCTAATTA AGATAGATTAGTGAAGCCACAGATGTAATCTAT CTTAATTAGCCACCCATGCCTACTGCCTCGGA | SEQ ID NO: 7 |
| CYP19A1 | 1588 | TGCTGTTGACAGTGAGCGAAGAACCAGGCTAC AAGAGAAATAGTGAAGCCACAGATGTATTTCTC TTGTAGCCTGGTTCTCTGCCTACTGCCTCGGA | SEQ ID NO: 4 |
| CYP11A1 | 1583 | TGCTGTTGACAGTGAGCGACCTGCAGAGATATC TTGTAAATAGTGAAGCCACAGATGTATTTACAA GATATCTCTGCAGGGTGCCTACTGCCTCGGA | SEQ ID NO: 2 |
| CYP21A2 | 1589 | CCGGCGACAACTTAATGCCTGCCTACTCGAGTA GGCAGGCATTAAGTTGTCGTTTTTG | SEQ ID NO: 1 |
| 3-βHSD1 | 3283 | CCGGCGCCTGTATCATTGATGTCTTCTCGAGAA GACATCAATGATACAGGCGTTTTTG | SEQ ID NO: 5 |
| StAR | 6770 | CCGGGCTGCCCAAGAGCATCATCAACTCGAGTT GATGATGCTCTTGGGCAGCTTTTTG | SEQ ID NO: 8 |
| HMGR | 3156 | CCGGGCAGTGATAAAGGAGGCATTTCTCGAGA AATGCCTCCTTTATCACTGCTTTTTG | SEQ ID NO: 9 |
| CYP11B1 | 1584 | CCGGCCCTCAACAGTACACCAGCATCTCGAGAT GCTGGTGTACTGTTGAGGGTTTTTG | SEQ ID NO: 11 |
| CYP11B2 | 1585 | CCGGCCTCACTTTCAGAGCGATTAACTCGAGTT AATCGCTCTGAAAGTGAGGTTTTTG | SEQ ID NO: 10 |
| 5α-Reductase 2 | 6716 | CCGGCCTCAAGATGTTTGAGGACTACTCGAGTA GTCCTCAAACATCTTGAGGTTTTTG | SEQ ID NO: 12 |
| SULT1E1 | 6783 | CCGGCCAGAAATTGTCGCCCTTCATCTCGAGAT GAAGGGCGACAATTTCTGGTTTTTG | SEQ ID NO: 13 |

TABLE 2-continued shRNA sequences used in this study*

| Gene Name | Gene ID | shRNA Sequence | |
|---|---|---|---|
| CYP3A4 | 1576 | CCGGCCTTACATATACACACCCTTTCTCGAGAA AGGGTGTGTATATGTAAGGTTTTG | SEQ ID NO: 14 |
| UGT1A1 | 54658 | CCGGCCCACTGTATTCTTCTTGCATCTCGAGATG CAAGAAGAATACAGTGGGTTTTG | SEQ ID NO: 15 |

*The sequences of the shRNA molecules are available online (http://www.openbiosystems.com) (Thermo Scientific Open Biosystems, Huntsville, AL USA).

TABLE 3

Examples of Test Substances

| Name | CAS# | Mode of action | Product class | Effect type |
|---|---|---|---|---|
| 2,4-Dinotrophenol | 51-28-5 | Cell toxicant: phosphorylation uncoupler | Industrial chemical | No known endocrine function other than cell toxicity and altered bioenergetics. |
| Aminoglutethimide | 125-84-8 | Inhibits CYP19 aromatase and other cytochrome P450 enzymes | Pharmaceutical (phased out) | Medium to weak inhibitor of T and E2 production. |
| Atrazine | 1912-24-9 | Aromatase inducer in vitro | Herbicide | Weak inducer of E2 production. |
| Benomyl | 17804-35-2 | Aromatase inducer in vitro | Fungicide | Weak inhibitor of T production; Weak inducer or negative for E2 production. Has been shown to induce aromatase activity in human ovarian tumor cells (KGN). |
| Bisphenol A | 80-05-7 | Cyclic-AMP second messenger system; proported ER binder | Monomer in polycarbonate plastics | Some evidence that alters Progesterone in vitro, but mechanism may or may not be c-AMP second messenger system. Medium to weak inhibitor of testosterone and inducer of estradiol. Tested positive for ER binding in vitro and in uterrotrophic assay. |
| Danazol | 17230-88-5 | 3HSD; P450c17 (17 hydrolase/C17-20 lyase); 17KSR | Agricultural Chemical, Antineoplastic agents, Contraceptives, postcoital, synthetic, Drug/ Therapeutic Agent | Negative for effects on testosterone; medium to strong inhibitor of estradiol. |
| Di (2-ethylhexyl) phthalate (DEHP) | 117-81-7 | Inhibits FSH-stimulated cAMP accumulation. Effects have been demonstrated at the level of P450scc and aromatase. Note: Compound that has been hypothesized to be active is the metabolite MEHP, not DEHP. | Polyvinyl additive | Metabolite monoethylhexyl phthalate (MEHP) has been shown to suppress aromatase and estradiol production in female rat primary granulosa cells. Parent compound is not considered active.; Negative for effects on testosterone but medium to strong inducer of estradiol in H295R cells. |
| Dimethoate | 60-51-5 | Inhibits steroidogenesis by disrupting transcription of StAR | Organophosphorus insecticide | Has been shown to decrease progesterone synthesis in vitro; does not affect aromatase activity in vitro; increases testosterone and estradiol in the H295R cells. |
| Ethane dimethane sulfonate (EDS) | 4672-49-5 | Cytotoxic | | No effect expected at non-cytotoxic concentrations. |
| Fenarimol | 60168-88-9 | Aromatase inhibition | Fungicide | Shown to inhibit aromatase (CYP19) in vitro, evidence from in vivo studies not as unequivocal; weak inhibitor of estradiol. |
| Finasteride | 98319-26-7 | 5-a reductase inhibitor | Pharmaceutical, therapeutic agent for prostrate cancer, hirsutism, and alopecia | Weak inhibitor of testosterone; negative for effects on estradiol. |

TABLE 3-continued

Examples of Test Substances

| Name | CAS# | Mode of action | Product class | Effect type |
|---|---|---|---|---|
| Flutamide | 13311-84-7 | P450c17 (17 hydrolase/C17-20lyase) | Pharmaceutical | Negative for effects on testosterone; weak inducer of estradiol. |
| Forskolin | 66575-29-9 | Cyclic-AMP second messenger system | Pharmaceutical | Strong inducer of T and E2 production. |
| Genistein | 446-72-0 | Anti-oxidant, topoisomerase inhibitor/tyrosine kinase inhibitor | Pharmaceutical | Medium inducer of E2 and weak inhibitor of T production. Weak estrogen receptor agonist |
| Glyphosate (Roundup) | 1071-83-6 | | Herbicide | Unknown. Has not shown to conclusively affect reproduction in laboratory in vivo studies. |
| Human chorionic gonadotropin (hcG) | 9002-61-3 | Binds to GtH receptor | Peptide hormone | No effect on T and E2 production in H295R cells. |
| Ketoconazole | 65277-42-1 | Inhibiting the microsomal cytochrome P450 mixed function oxidases. This drug inhibits 17 alpha-hydroxylase, C17-20 lyase, and the cholesterol-side-chain cleavage enzyme | Fungicide | Strong inhibitor of T production; Medium to weak inhibitor of E2 production; Induces progesterone production. |
| Letrozole | 112809-51-5 | Specifically inhibits catalytic aromatase activity. | Pharmaceutical | Strong inhibitor of E2 production. Weak inhibitor of T production. |
| Molinate | 2212-67-1 | Anti-cholinesterase/neurotoxicant. Note: In vitro, molinate is a poor inhibitor of esterase activity, whereas molinate sulfoxide, a major metabolite of molinate in rats, and molinate sulfone were shown to be potent inhibitors of esterase activity, suggesting that metabolic activation of molinate is required in vivo. | Pesticide | Weak inducer of E2 and negative/weak inhibitor of T production. |
| Nonoxynol-9 | 26027-38-3 | Unknown | Excipients, Pharmaceutical aid [surfactant], Pharmaceutical aid [wetting and or solubilizing agent], Spermaticide | Negative for effects on testosterone and estradiol. |
| Paraben (Butyl paraben) | 94-26-8 | ER binder | Preservative in food, cosmetics, toiletries, pharmaceutical. | Weak inducer of E2, and weak inhibitor of T production. |
| Piperonyl butoxide | 51-03-6 | Cytochrome P450 inhibitor | Pesticide synergist | This compound is used to inhibit several P450s involved in metabolism but not necessarily steroidogenesis; weak inhibitor of testosterone and weak inducer of estradiol. |
| Prochloraz | 67747-09-5 | General inhibitor of microsomal cytochrome P450 mixed function oxidases. | Fungicide | Strong inhibitor of T and E2 production. |
| Prometon | 1610-18-0 | Photosynthetic inhibitor | Wide-spectrum herbicide | Weak inducer of E2 production; Negative for T. |
| RU-486/mifepristone | 84371-65-3 | Negative for ER very weakly positive for AR at high conc., blocking the progesterone receptor, incr. levels of EST. | Pharmaceutical | Negative for effects on testosterone; medium to strong inducer of estradiol. |
| Spironolactone | 52-01-7 | Antiandrogen action through inhibition of 17α hydroxylase; Glucocorticoid & PXR-ligand | Pharmaceutical | Unknown |
| Trilostane | 13647-35-3 | 3B-HSD competitive inhibitor | Pharmaceutical, used in treatment of Cushings disease | Strong inducer of T and E2 production. |
| Vinclozolin | 50471-44-8 | Metabolized to Mi and M2, which are strong AR antagonists | Fungicide | Weak inducer of and moderate inhibitor of T production. |

TABLE 4

Fold change of basal steroid hormones production in culture medium of stable H295R/CYP21A KD cells comparing to unaltered H295R cells. Cell culture medium from each well of 24-well plate was replaced with new culture medium 24 h after cell seeding. By the end of 48 h further incubation, the culture medium from each well was collected for LC\MS-MS measurement.

| Steroid | Fold Change |
|---|---|
| Progesterone | 1.19 ± 0.08 |
| Testosterone (T) | 9.41 ± 3.05* |
| Estrone (E1) | 14.02 ± 1.36* |
| Estradiol (E2) | 17.78 ± 2.0* |

*significance level <0.001

TABLE 5

Expected cell properties of the newly established knockdown cell lines

| NO | Knockdown Gene | Entrez gene ID | Expected cell properties |
|---|---|---|---|
| 1 | CYP11A1 | 1583 | Decreased production of most steroids including prognenolone, progesterone, and T, E1, E2, etc. |
| 2 | CYP17A1 | 1586 | Increased production of Pregnenolone, progesterone and aldosterone, while decreased cortisol and sex steroids (AD, T, E1 and E2) production |
| 3 | CYP19A1 | 1588 | Decreased production of E1 and E2. |
| 4 | CYP21A2 | 1589 | Increased production of Pregnenolone, progesterone and sex steroids (AD, T, E1 and E2), but decreased aldosterone, and cortisol production |
| 5 | 3-βHSD1 | 3283 | Increased pregnenolone production, but decreased production of progesterone aldosterone, cortisol and sex steroids (AD, T, E1 and E2) |
| 6 | 3-βHSD2 | 3284 | Increased pregnenolone production, but decreased production of progesterone aldosterone, cortisol and sex steroids (AD, T, E1 and E2) |
| 7 | 17-βHSD1 | 3292 | Increased production of AD and E1, but decreased T and E2 |
| 8 | StAR | 6770 | Decreased production of most steroids including prognenolone, progesterone, and T, E1, E2, etc. |
| 9 | HMGR | 3156 | Decreased production of most steroids including prognenolone, progesterone, and T, E1, E2, etc. |
| 10 | CYP11B1 | 1584 | Decreased production of cortisol |
| 11 | CYP11B2 | 1585 | Decreased production of corticosterone and aldosterone |
| 12 | 5α-Reductase 2 | 6716 | Increased production of T, but decreased dihydrotestosterone |
| 13 | SULT1E1 | 6783 | Increased production of most steroids including prognenolone, progesterone, and T, E1, E2, etc. |
| 14 | CYP3A4 | 1576 | Increased production of most steroids including prognenolone, progesterone, and T, E1, E2, etc. |
| 15 | UGT1A1 | 54658 | Increased production of most steroids including prognenolone, progesterone, and T, E1, E2, etc. |

TABLE 6

Basal production of steroids in three different steroidogenic cell lines

| Cell line | H295R | JEG-3 | R2C |
|---|---|---|---|
| 21a Hydroxyprogesterone | 29.90(4.85) | ND | 20.13(6.38) |
| 17a Hydroxyprogesterone | 6.68(0.50) | ND | 47.07(10.96) |
| Corticosterone | 27.73(2.81) | ND | 6.13(1.49) |
| Androstenedione | 121.67(20.23) | ND | 0.55(0.21) |
| Testosterone | 1.80(0.16) | ND | 0.31(0.11) |
| Estone | 0.76(0.03) | ND | 20.10(4.53) |
| Estradiol | 0.15(0.03) | 1.13(0.12) | 9.20(1.08) |

CITATIONS FOR REFERENCES REFERRED TO IN THE SPECIFICATION

1. Gazdar, A. F., Oie, H. K., Shackleton, C. H., Chen, T. R., Triche, T. J., Myers, C. E., Chrousos, G. P., Brennan, M. F., Stein, C. A., and La Rocca, R. V. (1990). Establishment and characterization of a human adrenocortical carcinoma cell line that expresses multiple pathways of steroid biosynthesis. Cancer Res 50(17), 5488-5496.
2. Gracia, T., Hilscherova, K., Jones, P. D., Newsted, J. L., Zhang, X., Hecker, M., Higley, E. B., Sanderson, J. T., Yu, R. M. K., Wu, R. S. S., and Giesy, J. P. (2006). The H295R system for evaluation of endocrine-disrupting effects. Ecotoxicology and Environmental Safety 65(3), 293-305.
3. Hecker, M., Newsted, J. L., Murphy, M. B., Higley, E. B., Jones, P. D., Wu, R., and Giesy, J. P. (2006). Human adrenocarcinoma (H295R) cells for rapid in vitro determination of effects on steroidogenesis: hormone production. Toxicol. Appl. Pharmacol 217(1), 114-124.
4. Hilscherova, K., Jones, P. D., Gracia, T., Newsted, J. L., Zhang, X. W., Sanderson, J. T., Yu, R. M. K., Wu, R. S. S., and Giesy, J. P. (2004). Assessment of the effects of chemicals on the expression of ten steroidogenic genes in the H295R cell line using real-time PCR. Toxicol. Sci. 81(1), 78-89.
5. Kavlock, R. J., Daston, G. P., DeRosa, C., Fenner-Crisp, P., Gray, L. E., Kaattari, S., Lucier, G., Luster, M., Mac, M. J., Maczka, C., Miller, R., Moore, J., Rolland, R., Scott, G., Sheehan, D. M., Sinks, T., and Tilson, H. A. (1996).

Research needs for the risk assessment of health and environmental effects of endocrine disruptors: a report of the U.S. EPA-sponsored workshop. Environ. Health Perspect. Suppl 4, 715-740.
6. Sanderson, J. T. (2006). The steroid hormone biosynthesis pathway as a target for endocrine-disrupting chemicals. Toxicol. Sci. 94(1), 3-21.
7. Sanderson, J. T., Boerma, J., Lansbergen, G. W. A., and van den Berg, M. (2002). Induction and inhibition of aromatase (CYP19) activity by various classes of pesticides in H295R human adrenocortical carcinoma cells. Toxicology and Applied Pharmacology 182(1), 44-54.
8. Staels, B., Hum, D. W., and Miller, W. L. (1993). Regulation of steroidogenesis in NCI-H295 cells: a cellular model of the human fetal adrenal. Mol Endocrinol 7(3), 423-433.
9. Zhang, X., Yu, R. M., Jones, P. D., Lam, G. K., Newsted, J. L., Gracia, T., Hecker, M., Hilscherova, K., Sanderson, T., Wu, R. S., and Giesy, J. P. (2005). Quantitative RT-PCR methods for evaluating toxicant-induced effects on steroidogenesis using the H295R cell line. Environ. Sci. Technol. 39(8), 2777-2785.
10. Zhang, X., Moore, J. N., Newsted, J. L., Hecker, M., Zwiernik, M. J., Jones, P. D., Bursian, S. J., and Giesy, J. P. (2009). Sequencing and characterization of mixed function monooxygenase genes CYP1A1 and CYP1A2 of Mink (*Mustela vison*) to facilitate study of dioxin-like compounds. Toxicology and Applied Pharmacology 234(3), 306-313.
11. Merino, P., Bachega, T., Cespedes, P., Trejo, L., Billerbeck, A. E., and Codner, E. (2007). [Molecular study of CYP21A2 gene for prenatal diagnosis of congenital adrenal hyperplasia. Report of a family]. Rev. Med. Chil. 135 (11), 1450-1455.
12. Hecker M, Newsted J L, Murphy M B, Higley E B, Jones P D, Wu R, Giesy J P (2006a) Toxicol Appl Pharmacol 217:114-124.
13. Hilscherova K, Jones P D, Gracia T, Newsted J L, Zhang X, Sanderson J T, Yu R M K, Wu R S S, Giesy J P (2004) Toxicol Sci 81:78-89.
14. Sanderson, J. T., Boerma, J., Lansbergen, G., and Van den Berg, M. (2002) Toxicol. Appl. Pharmacol. 182, 44-54.
15. Gazdar A F, Oie H K, Shackleton C H, Chen, T R, Triche, T J, Myers C E, Chrousos G P, Brennan M F, Stein C A., La Rocca R V (1990) Cancer Res 50:5488-5496.
16. Rainey, W. E., Bird, I. M., Sawetawan, C., Hanley, N. A., Mccarthy, J. L., Mcgee, E. A., Wester, R., and Mason, J. I. (1993) J. Clin. Endocrinol. Metab. 77, 731-737.
17. Puddefoot, J. R., Barker, S., Glover, H. R., Malouitre, S. D. M., Vinson, G. P. (2002) Noncompetitive steroid inhibition of estrogen receptor functions. Int J Cancer 101:17-22.
18. Mosman, T., 1983. Rapid colorimetric assay for growth and survival: application to proliferation and cytotoxicity. J. Immunol. Methods. 100, 45-50.
19. Battelle. (March 2005) Detailed Review Paper on Steroidogenesis. Available at http://www.epa.gov/endo/pubs/edmvs/steroidogenesis_drp_final_3_29_05.pdf
20. OECD Conceptual Framework for the Testing and Assessment of Endocrine Disrupting Chemicals http://www.oecd.org/document/58/0,3343,en_2649_34377_2348794_1_1_1_1,00.html
21. OECD 2002. Detailed Review Paper: Appraisal of Test Methods for Sex Hormone Disrupting Chemicals. OECD Series on Testing and Assessment No. 21. ENV/JM/MONO (2002)8.
22 Rainey, W. E.; Bird, I. M.; Mason, J. I. The NCI-H295 cell line: a pluripotent model for human adrenocortical studies. *Mol. Cell Endocrionol.* 1994, 100, 45-50.
23 Zhang, X., Newsted, J. L., Hecker, M., Higley, E. B., Jones, P. D., and Giesy, J. P. (2009). Classification of chemicals based on concentration-dependent toxicological data using ToxClust. *Environ. Sci. Technol.* 43(10), 3926-3932.
24 A. Lancon, D. Delma, H. Osman, J. P. Thenot, B. Jannin and N. Latruffe, Human hepatic cell uptake of resveratrol: involvement of both passive diffusion and carrier-mediated process, *Biochem Biophys Res Commun* 316 (2004), pp. 1132-1137.

---

The invention claimed is:

1. A screening assay for identifying an endocrine disruptor comprising:
    a) contacting with a test substance a steroidogenesis modified cell comprising a CYP21A2 steroid biosynthesis knock down nucleic acid that reduces expression of CYP21A2 and the cell comprises reduced expression of said gene;
    b) determining a level of at least one steroid or steroidogenic gene mRNA or steroidogenic gene enzyme activity in the cell contacted with the test substance and comparing the level to a control; and
    c) identifying the test substance as an endocrine disruptor if the level of the at least one steroid or steroidogenic gene mRNA or steroidogenic gene enzyme activity determined in step b) is increased or decreased compared to the control.

2. The screening assay of claim 1, wherein the at least one steroid in step b) is selected from androstenedione (A), testosterone (T), dihydrotestosterone (DHT), estrone (E1) and/or 17β estradiol (E2).

3. The screening assay of claim 1, wherein the test substance is selected from industrial chemicals, pharmaceuticals, herbicides, fungicides, polycarbonate plastic monomers, agricultural chemicals, antineoplastic agents, contraceptives, postcoitals, synthetics, drugs, therapeutic agents, polyvinyl additives, organophosphorus insecticides, peptide hormones, excipients, pharmaceutical aids, spermaticides, food preservatives, cosmetics, toiletries, and pesticide synergists.

4. The screening assay of claim 1, wherein the level of the at least one steroid determined in step b) is determined by LC-MS, GC-MS, ELISA, optionally automated ELISA, or immunoblotting.

5. The screening assay of claim 1, wherein the test substance is identified as an endocrine disruptor if the level of the at least one steroid or steroidogenic gene mRNA or steroidogenic gene enzyme activity determined in step b) is increased or decreased by at least 10%, at least 15%, at least 20%, at least 25%, at least 30%, at least 35%, at least 40%, at least 45%, at least 50% at least 55%, at least 60%, at least 65%, at least 70%, at least 80%, at least 85%, or at least 90% compared to the control.

6. The screening assay of claim 1 wherein the CYP21A2 steroid biosynthesis knock down nucleic acid reduces the expression of CYP21A2 by antisense technology and/or by homologous recombination.

7. The screening assay of claim 1 wherein the CYP21A2 steroid biosynthesis knock down nucleic acid comprises a siRNA nucleic acid, a shRNA nucleic acid or an antisense nucleic acid.

8. The screening assay of claim 7, wherein the CYP21A2 steroid biosynthesis knock down nucleic acid is operatively linked to a promoter.

9. The screening assay of claim 8, wherein the CYP21A2 steroid biosynthesis knock down nucleic acid comprises SEQ ID NO:1.

10. The screening assay of claim 8, wherein the steroidogenesis modified cell is an isolated steroidogenesis H295, H295R, JEG-3 or R2C modified cell.

11. The screening assay of claim 8, wherein the steroidogenesis modified cell, prior to contact with the test substance, expresses at least 10%, at least 15%, at least 20%, at least 25%, at least 30%, at least 35%, at least 40%, at least 45%, at least 50% at least 55%, at least 60%, at least 65%, at least 70%, at least 80%, at least 85%, or at least 90% less of CYPA21A2 compared to an unmodified cell.

12. The screening assay of claim 8, wherein the steroidogenesis modified cell, prior to contact with the test substance, produces an increased basal level of at least one steroid compared to an unmodified cell.

13. The screening assay of claim 12, wherein the at least one steroid produced at an increased basal level is selected from androstenedione (AD), testosterone (T), dihydrotestosterone (DHT), estrone (E1) and/or 17β estradiol (E2).

14. The screening assay of claim 12, wherein the basal level of the at least one steroid is increased by at least 10%, at least 15%, at least 20%, at least 25%, at least 30%, at least 35%, at least 40%, at least 45%, at least 50% at least 55%, at least 60%, at least 65%, at least 70%, at least 80%, at least 85%, or at least 90% compared to the unmodified cell or is at least 2×, at least 3×, at least 4×, at least 5×, at least 6×, at least 7×, at least 8×, at least 9×, at least 10×, at least 11×, at least 12×, at least 15×, at least 20×, at least 25×, at least 30×, at least 40×, at least 50×, at least 60×, at least 70×, at least 80×, at least 90×, at least 100×, at least 125×, at least 150×, at least 175×, at least 200×, or more compared to the unmodified cell.

15. The screening assay of claim 13, wherein the steroidogenesis modified cell, prior to contact with the test substance, produces a basal level of at least 10 pg/ml, at least 20 pg/ml, at least 30 pg/ml, at least 40 pg/ml, at least 50 pg/ml, at least 60 pg/ml, at least 70 pg/ml, at least 80 pg/ml, at least 90 pg/ml, at least 100 pg/ml, at least 125 pg/ml, at least 150 pg/ml, at least 175 pg/ml, at least 200 pg/ml, at least 250 pg/ml, at least 300 pg/ml, at least 350 pg/ml, at least 400 pg/ml, at least 500 pg/ml, at least 600 pg/ml, at least 800 pg/ml, or at least 1,000 pg/ml of 17β-estradiol; at least 1 attog/cell per 48 hrs, at least 3 attog/cell per 48 hrs, at least 10 attog/cell per 48 hrs, at least 20 attog/cell per 48 hrs, at least 30 attog/cell per 48 hrs, or at least 100 attog/cell per 48 hrs of E2; at least 1 femtog/cell per 48 hrs, at least 3 femtog/cell per 48 hrs, at least 5 femtog/cell per 48 hrs, at least 10 femtog/cell per 48 hrs, at least 20 femtog/cell per 48 hrs, at least 30 femtog/cell per 48 hrs, at least 40 femtog/cell per 48 hrs or at least 200 femtog/cell per 48 hrs of testosterone; between about 10 femtog/cell per 48 hrs and about 500 femtog/cell per 48 hrs of androstenedione; and/or between about 1 femtog/cell per 48 hrs and about 100 femtog/cell per 48 hrs of estrone, compared to the unmodified cell.

16. The screening assay of claim 8, wherein the steroid biosynthesis knock down nucleic acid operatively linked to a promoter is comprised in a lentiviral plasmid construct.

17. The screening assay of claim 8, wherein the at least one steroid in step b) is selected from androstenedione (A), testosterone (T), dihydrotestosterone (DHT), estrone (E1) and/or 17β estradiol (E2).

18. The screening assay of claim 8, wherein the test substance is selected from industrial chemicals, pharmaceuticals, herbicides, fungicides, polycarbonate plastic monomers, agricultural chemicals, antineoplastic agents, contraceptives, postcoitals, synthetics, drugs, therapeutic agents, polyvinyl additives, organophosphorus insecticides, peptide hormones, excipients, pharmaceutical aids, spermaticides, food preservatives, cosmetics, toiletries, and pesticide synergists.

19. The screening assay of claim 8, wherein the level of the at least one steroid determined in step b) is determined by LC-MS, GC-MS, ELISA, optionally automated ELISA, or immunoblotting.

20. The screening assay of claim 8, wherein the test substance is identified as an endocrine disruptor if the level of the at least one steroid or steroidogenic gene mRNA or steroidogenic gene enzyme activity determined in step b) is increased or decreased by at least 10%, at least 15%, at least 20%, at least 25%, at least 30%, at least 35%, at least 40%, at least 45%, at least 50% at least 55%, at least 60%, at least 65%, at least 70%, at least 80%, at least 85%, or at least 90% compared to the control.

21. The screening assay of claim 8, wherein the steroidogenesis modified cell is an isolated steroidogenesis modified H295R cell.

22. The screening assay of claim 21, wherein the CYP21A2 steroid biosynthesis knock down nucleic acid comprises SEQ ID NO:1.

23. The screening assay of claim 21, wherein the steroidogenesis modified cell, prior to contact with the test substance, expresses at least 10%, at least 15%, at least 20%, at least 25%, at least 30%, at least 35%, at least 40%, at least 45%, at least 50% at least 55%, at least 60%, at least 65%, at least 70%, at least 80%, at least 85%, or at least 90% less of CYP21A2 compared to an unmodified cell.

24. The screening assay of claim 21, wherein the steroidogenesis modified cell, prior to contact with the test substance, produces an increased basal level of at least one steroid compared to an unmodified cell.

25. The screening assay of claim 24, wherein the at least one steroid produced at an increased basal level is selected from androstenedione (AD), testosterone (T), dihydrotestosterone (DHT), estrone (E1) and/or 17β estradiol (E2).

26. The screening assay of claim 24 wherein the basal level of the at least one steroid is increased by at least 10%, at least 15%, at least 20%, at least 25%, at least 30%, at least 35%, at least 40%, at least 45%, at least 50% at least 55%, at least 60%, at least 65%, at least 70%, at least 80%, at least 85%, or at least 90% compared to the unmodified cell or is at least 2×, at least 3×, at least 4×, at least 5×, at least 6×, at least 7×, at least 8×, at least 9×, at least 10×, at least 11×, at least 12×, at least 15×, at least 20×, at least 25×, at least 30×, at least 40×, at least 50×, at least 60×, at least 70×, at least 80×, at least 90×, at least 100×, at least 125×, at least 150×, at least 175×, at least 200×, or more compared to the unmodified cell.

27. The screening assay of claim 24, wherein the steroidogenesis modified cell, prior to contact with the test substance, produces a basal level of at least 10 pg/ml, least 20 pg/ml, at least 30 pg/ml, at least 40 pg/ml, at least 50 pg/ml at least 60 pg/ml, at least 70 pg/ml, at least 80 pg/ml, at least 90 pg/ml, at least 100 pg/ml, at least 125 pg/ml, at least 150 pg/ml, at least 175 pg/ml, at least 200 pg/ml, at least 250 pg/ml, at least 300 pg/ml, at least 350 pg/ml, at least 400 pg/ml, at least 500 pg/ml, at least 600 pg/ml, at least 800 pg/ml, or at least 1,000 pg/ml of 17β-estradiol; at least 1 attog/cell per 48 hrs, at least 3 attog/cell per 48 hrs, at least 10 attog/cell per 48 hrs, at least 20 attog/cell per 48 hrs, at least 30 attog/cell per 48 hrs, or at least 100 attog/cell per 48 hrs of E2; at least 1 femtog/cell per 48 hrs, at least 3 femtog/cell per 48 hrs, at least 5 femtog/cell per 48 hrs, at least 10 femtog/cell per 48 hrs, at least 20 femtog/cell per 48 hrs, at least 30 femtog/cell per 48 hrs, at least 40 femtog/cell per 48 hrs or at least 200 femtog/cell per 48 hrs of testosterone; between about 10 femtog/cell per 48 hrs and about 500 femtog/cell per 48 hrs of androstenedione; and/or between about 1 femtog/cell per 48 hrs and about 100 femtog/cell per 48 hrs of estrone, compared to the unmodified cell.

28. The screening assay of claim 21, wherein the steroid biosynthesis knock down nucleic acid operatively linked to a promoter is comprised in a lentiviral plasmid construct.

29. The screening assay of claim 21, wherein the at least one steroid in step b) is selected from androstenedione (A), testosterone (T), dihydrotestosterone (DHT), estrone (E1) and/or 17β estradiol (E2).

30. The screening assay of claim 21, wherein the test substance is selected from industrial chemicals, pharmaceuticals, herbicides, fungicides, polycarbonate plastic monomers, agricultural chemicals, antineoplastic agents, contraceptives, postcoitals, synthetics, drugs, therapeutic agents, polyvinyl additives, organophosphorus insecticides, peptide hormones, excipients, pharmaceutical aids, spermaticides, food preservatives, cosmetics, toiletries, and pesticide synergists.

31. The screening assay of claim 21, wherein the level of the at least one steroid determined in step b) is determined by LC-MS, GC-MS, ELISA, optionally automated ELISA, or immunoblotting.

32. The screening assay of claim 21, wherein the test substance is identified as an endocrine disruptor if the level of the at least one steroid or steroidogenic gene mRNA or steroidogenic gene enzyme activity determined in step b) is increased or decreased by at least 10%, at least 15%, at least 20%, at least 25%, at least 30%, at least 35%, at least 40%, at least 45%, at least 50% at least 55%, at least 60%, at least 65%, at least 70%, at least 80%, at least 85%, or at least 90% compared to the control.

33. A kit for screening for an endocrine disruptor comprising a steroidogenesis modified cell comprising a CYP21A2 steroid biosynthesis knock down nucleic acid that reduces expression of CYP21A2 and a component for determining the level of at least one steroid.

34. The kit of claim 33, wherein the steroidogenesis modified cell is a steroidogenesis modified H295R cell and/or wherein the steroid biosynthesis knock down nucleic acid comprises SEQ ID NO: 1.

* * * * *

UNITED STATES PATENT AND TRADEMARK OFFICE
CERTIFICATE OF CORRECTION

PATENT NO. : 8,501,401 B2
APPLICATION NO. : 13/619236
DATED : August 6, 2013
INVENTOR(S) : Xiaowei Zhang, Markus Hecker and P. Giesy It is certified that error appears in the above-identified patent and that said Letters Patent is hereby corrected as shown below:

In the Claims:

Col. 52, in claim 27, line 64 "least 20 pg/ml" should read "at least 20 pg/ml"

Signed and Sealed this
Fifteenth Day of October, 2013

Teresa Stanek Rea
*Deputy Director of the United States Patent and Trademark Office*